US006844477B2

(12) United States Patent
Dahl et al.

(10) Patent No.: US 6,844,477 B2
(45) Date of Patent: *Jan. 18, 2005

(54) PROCESSES FOR THE PURIFICATION OF HIGHER DIAMONDOIDS AND COMPOSITIONS COMPRISING SUCH DIAMONDOIDS

(75) Inventors: Jeremy E. Dahl, Palo Alto, CA (US); Robert M. Carlson, Petaluma, CA (US)

(73) Assignee: Chevron U.S.A. Inc., San Ramon, CA (US)

(*) Notice: Subject to any disclaimer, the term of this patent is extended or adjusted under 35 U.S.C. 154(b) by 400 days.

This patent is subject to a terminal disclaimer.

(21) Appl. No.: 10/017,821

(22) Filed: Dec. 12, 2001

(65) Prior Publication Data

US 2002/0193648 A1 Dec. 19, 2002

Related U.S. Application Data

(60) Provisional application No. 60/262,842, filed on Jan. 19, 2001.

(51) Int. Cl.[7] .......................... C07C 13/28; C07C 7/00
(52) U.S. Cl. .......................... 585/352; 585/16; 585/21; 585/800; 585/802; 585/803; 117/68; 117/69; 117/70
(58) Field of Search ........................ 585/803, 21, 16, 585/800, 352, 802; 117/68, 69, 70

(56) References Cited

U.S. PATENT DOCUMENTS

| | | | |
|---|---|---|---|
| 3,457,318 A | 7/1969 | Capaldi | |
| 3,832,332 A | 8/1974 | Thompson | |
| 4,952,748 A | 8/1990 | Alexander | |
| 4,952,749 A | 8/1990 | Alexander | |
| 4,952,757 A | 8/1990 | Purcell | |
| 4,982,049 A | 1/1991 | Alexander | |
| 5,017,734 A | 5/1991 | Baum | |
| 5,019,665 A | 5/1991 | Partridge | |
| 5,245,104 A | 9/1993 | Cullick | |
| 5,268,513 A | 12/1993 | Shen | |
| 5,298,666 A | 3/1994 | Shen | |
| 5,306,851 A | * 4/1994 | Wu et al. | ............... 585/22 |
| 5,334,228 A | * 8/1994 | Ashjian et al. | ........... 44/347 |
| 5,347,063 A | 9/1994 | Shen | |
| 5,369,213 A | 11/1994 | Shen | |
| 5,380,947 A | 1/1995 | Chen | |
| 5,382,684 A | 1/1995 | Moini | |
| 5,394,733 A | 3/1995 | Acholla | |
| 5,397,488 A | 3/1995 | Chen | |
| 5,410,092 A | 4/1995 | Shen | |
| 5,414,189 A | * 5/1995 | Chen et al. | .......... 585/801 |
| 5,430,193 A | 7/1995 | Shen | |
| 5,461,184 A | 10/1995 | Swanson | |
| 5,498,812 A | 3/1996 | Bradway | |
| 5,576,355 A | 11/1996 | Chen | |
| 6,235,851 B1 | 5/2001 | Ishii | |

FOREIGN PATENT DOCUMENTS

| | | |
|---|---|---|
| EP | 0399851 | 11/1996 |
| WO | WO 95/06019 | 3/1995 |
| WO | WO 95/11472 | 4/1995 |

OTHER PUBLICATIONS

Aczel, et al., "Stability of Adamantane and its Derivatives to Coal–liquefaction Conditions, and its implications toward the organic structure of Coal", *Fuel*, vol. 58, pp. 228–230, (Mar. 1979).

Balaban, et al., Systemic Classification and Nomenclature of Diamond Hydrocarbons–I, *Tetrahedron*, 34, pp. 3599–3606, (1978).

Badziag, P., et al., "Nanometre–sized Diamonds are More Stable than Graphite", *Nature*, vol. 343, pp. 244–245, and 517 (Jan. 1990).

Bagrii, Ye, et al., "Catalytic Breakdown of Paraffinic Hydrocarbons in the Presence of Adamantanes", *Petrol. Chem USSR*, vol. 30, No. 2, pp. 131–134, (1990), no month.

Chung, et al., Recent Development in High–Energy Density Liquid Fuels, *Energy and Fuels 13*, pp. 641–649, (1999), no month.

Dahl, J., et al., Diamondoid Hydrocarbons as Indicators of Natural Oil Cracking, *Nature, 399*, pp. 54–57, (1999), no month.

Drexler, Eric K., *Nanosystems: Molecular Machinery Manufacturing and Computation*, John Wiley & Sons, pp. 238–249, (1992), no month.

Fort, Jr., et al., Adamantane: Consequences of the Diamondoid Structure, *Chem. Rev., 64*, pp. 277–300, (1964), no month.

Hala, V.S., et al., "Analyse Unds erwendung on Pyrolyseol", *Jahrgang*, pp. 85–87, (Feb. 1971) In German—English Abstract on p. 85, considered to extent of english abstract.

Landa, S., "Adamantane and its Homologues", *Current Science*, Gangalore, India, Vo. 32, pp. 485–489 (1963), no month.

Lin, et al., Natural Occurrence of Tetramantane ($C_{22}H_{36}$), Pentamantane ($C_{26}H_{32}$), and Hexamantane ($C_{30}H_{36}$) in a Deep Petroleum Reservoir, *Fuel, 74*:10, pp. 1512–1521, (1995), no month.

McKervey, Synthetic Approaches to Large Diamondoid Hydrocarbonds, *Tetrahedron, 36*, pp. 971–992, (1980), no month.

(List continued on next page.)

*Primary Examiner*—Elizabeth D. Wood
(74) *Attorney, Agent, or Firm*—Burns, Doane, Swecker & Mathis, L.L.P.

(57) ABSTRACT

Disclosed are processes for the recovery and purification of higher diamondoids from a hydrocarbonaceous feedstock. Specifically disclosed is a multi-step recovery process for obtaining diamondoid compositions enhanced in tetramantane components and higher diamondoid components. Also disclosed are compositions comprising at least about 10 weight percent of non-ionized tetramantane components and higher diamondoid components and at least about 0.5 weight percent of non-ionized pentamantane components and higher diamondoid components based on the total weight of diamondoid components present.

39 Claims, 24 Drawing Sheets

OTHER PUBLICATIONS

Machacek, V., et al., "Let Od Objeveni Adamantanu", *Chemicke Listy/svazek*, pp. 753–761, (1982) Russian—English Abstract on p. 761, no month, considered to extent of english abstract.

Oya, A, et al., "Carbonization of Adamantanes to a Graphitizable Carbon", *Fuel*, vol. 69, pp. 667–669, (Aug. 1981).

Petrov, A., "Hydrocarbons of Adamantane Series as Indicies of Petroleum Catagenesis Process", *Advances in Organic Geo Chemistry*, 6$^{th}$ International Meeting on Organic Geochemistry, pp. 517–522 (1973), no month.

Prusova, D., Liquid Chromatography of Adamantanes and Carbon Absorbents, *J. Chrom.* 234, pp. 1–11, (1982), no month.

Rollman, L., et al., "Adamantanes From Petroleum, with Zeolites", American Chemical Study, 210$^{th}$ ACS National Meeting, Abstract and paper, Aug. 20, 1995.

Sandia National Laboratories (2000), World's First Diamond Micromachines Created at Sandia, Press Release, (Feb. 22, 2000), www.Sandia.gov.

Schleyer, P., et al., "Nonacyclo[$11.7.1.1^{2,18}.O^{3,16}.O^{4,13}.O^{5,10}.O^{6,14}.O^{7,11}.O^{15,20}$]–Docane, a Bastard Tetramantane", *J. of the Am. Chem. Soc.*, 90:8, letter to the editor, Aug. 28, 1968.

Shen, M., et al., Finite $T_d$ Symmetry Models for Diamond: From Adamantane to Superadamantane ($C_{35}H_{36}$), *J. Am., Chem. Soc.*, vol. 114, No. 2, pp 497–505, (1992), no month.

Supryadkina, NY, et al., "Catalytic Dealkylation of Alkyladamantanes", *Petrol. Chem., USSR*, vol. 28, No. 2, pp. 103–110, (1988), no month.

Tominaga, K., et al., "Next–generation Fine Chemicals Raw Material–Adamantane", *Chem Econ & Eng. Review*, vol. 17, No. 10, pp. 23–29, (Oct. 1985).

Vodicka, L, et al., "High Performance Liquid Chromatography of Halogeno Derivatives of Adamantane and Diamantane", *J. Chrom*, 270, pp. 199–205, (1983), no month.

Wingert, W., "G.c.–m.s. Analysis of Diamondoid Hydrocarbons in Smackover Petroleums", *Fuel*, vol. 71, pp. 37–42, (Jan. 1992).

* cited by examiner

* Atmospheric-Equivalent

First Column — Fraction 33

Second Column

GC Retention Time (min.)

mirror plane

[121] Tetramantane     [123] Tetramantane (ENANTIOMERS)     [1(2)3] Tetramantane HPLC Fr. 6 (TIC)

Tetramantane (m/z 292)

Time (min)

FIG. 30

| Number of Diamond Crystal Cage Units | Number of Molecular Formulae | Higher Diamondoid | Molecular Weights | | | | | | | |
|---|---|---|---|---|---|---|---|---|---|---|
| 4 | 1 | Tetramantane | 292 | | | | | | | |
| 5 | 2 | Pentamantane | 344 | 330 | | | | | | |
| 6 | 3 | Hexamantane | 396 | 382 | 342 | | | | | |
| 7 | 4 | Heptamantane | 448 | 434 | 394 | | | | | |
| 8 | 5 | Octamantane | 500 | 486 | 446 | 420 | | | | |
| 9 | 6 | Nonamantane | 552 | 538 | 498 | 420 | 432 | | | |
| 10 | 7 | Decamantane | 604 | 590 | 550 | 524 | 484 | 444 | | |
| 11 | 8 | Undecamantane | 656 | 642 | 602 | 576 | 536 | 496 | 456 | |
| | | | | | | | 588 | 548 | 508 | 534 |

FIG. 31

| Higher Diamondoid | Distillation Cuts Made on Atmospheric Resid of Feedstock B (°F) | | | | | | | | | |
|---|---|---|---|---|---|---|---|---|---|---|
| | 601-656 Fr.1 | 656-702 Fr.2 | 702-752 Fr.3 | 752-800 Fr.4 | 800-852 Fr.5 | 852-900 Fr.6 | 900-950 Fr.7 | 950-976 Fr.8 | 976-1000 Fr.9 | 1000-1026 Fr.10 |
| Tetramantanes | | | | | | | | | | |
| Pentamantanes | | | | | | | | | | |
| Cyclohexamantanes | | | | | | | | | | |
| Hexamantanes | | | | | | | | | | |
| Heptamantanes | | | | | | | | | | |
| Octamantanes | | | | | | | | | | |
| Nonamantanes | | | | | | | | | | |
| Decamantanes | | | | | | | | | | |
| Undecamantanes | | | | | | | | | | |

FIG. 33

PROCESSES FOR THE PURIFICATION OF HIGHER DIAMONDOIDS AND COMPOSITIONS COMPRISING SUCH DIAMONDOIDS

This application claims the benefit under 35 USC §119 to U.S. Provisional Application Ser. No. 60/262,842, filed Jan. 19, 2001 which application is incorporated herein by reference in its entirety.

BACKGROUND OF THE INVENTION

This invention is directed to novel processes for the recovery and at least partial purification of higher diamondoid components from hydrocarbonaceous feedstocks. Specifically, this invention is directed to recovery processes for obtaining compositions enhanced in one or more higher diamondoid components.

This invention is also directed to compositions comprising enriched levels of one or more higher diamondoids.

The following publications and patents are cited in this application as superscript numbers:

1. Fort, Jr., et al., *Adamantane: Consequences of the Diamondoid Structure*, Chem. Rev., :277–300 (1964)
2. Sandia National Laboratories (2000), *World's First Diamond Micromachines Created at Sandia*, Press Release, (Feb. 22, 2000) www.Sandia.gov.
3. Lin, et al., *Natural Occurrence of Tetramantane ($C_{22}H_{28}$),Pentamantane ($C_{26}H_{32}$) and Hexamantane ($C_{30}H_{36}$) in a Deep Petroleum Reservoir*, Fuel, (10) :1512–1521 (1995)
4. Chen, et al., Isolation of High Purity Diamondoid Fractions and Components, U.S. Pat. No. 5,414,189, issued May 9, 1995
5. Alexander, et al., Removal of Diamondoid Compounds from Hydrocarbonaceous Fractions, U.S. Pat. No. 4,952,747, issued Aug. 28, 1990
6. Alexander, et al., Purification of Hydrocarbonaceous Fractions, U.S. Pat. No. 4,952,748, issued Aug. 28, 1990
7. Alexander, et al., Removal of Diamondoid Compounds from Hydrocarbonaceous Fractions, U.S. Pat. No. 4,952,749, issued Aug. 28, 1990
8. Alexander, et al., Purification of Hydrocarbonaceous Fractions, U.S. Pat. No. 4,982,049, issued Jan. 1, 1991
9. Swanson, Method for Diamondoid Extraction Using a Solvent System, U.S. Pat. No. 5,461,184, issued Oct. 24, 1995
10. Partridge, et al., Shape-Selective Process for Concentrating Diamondoid-Containing Hydrocarbon Solvents, U.S. Pat. No. 5,019,665, issued May 28, 1991
11. Dahl, et al., Diamondoid *Hydrocarbons as Indicators of Natural Oil Cracking*, Nature, 54–57 (1999).
12. McKervey, Synthetic *Approaches to Large Diamondoid Hydrocarbons*, Tetrahedron, :971–992 (1980).
13. Wu, et al., High Viscosity Index Lubricant Fluid, U.S. Pat. No. 5,306,851, issued Apr. 26, 1994.
14. Chung et al., Recent *Development in High-Energy Density Liquid Fuels*, Energy and Fuels, 641–649 (1999).

All of the above publications and patents are herein incorporated by reference in their entirety to the same extent as if each individual publication or patent was specifically and individually indicated to be incorporated by reference in its entirety.

Diamondoids are cage-shaped hydrocarbon molecules possessing amazingly rigid structures that are superimposable fragments of the diamond crystal lattice[1] (see FIG. 1). Adamantane, a ten-carbon molecule, is the smallest member of the diamondoid series, consisting of one diamond crystal subunit. Diamantane contains two face-fused diamond subunits, triamantane three, tetramantane four, and so on. While there is only one isomeric form of adamantane, diamantane and triamantane, there are four different isomeric tetramantanes; four different shapes containing four diamond subunits that can be superimposed on the diamond crystal lattice. Two of these isomers are enantiomeric (mirror images of each other). The number of possible isomers increases rapidly with each higher member of the diamondoid series. Because diamondoid crystal units can share more than a single face in some higher diamondoids, hydrogen to carbon ratios, i.e., the degree of condensation, also show increasing variation resulting in an increasing variety of molecular weights for each successive higher diamondoid family. FIG. 30 is a table depicting the range of higher diamondoids.

The parent diamondoids may be substituted with alkyls at various sites, and a myriad of methyl, ethyl, dimethyl, trimethyl, propyl, etc., substituted species are possible and occur naturally in petroleum feedstocks along with the parent diamondoids. Diamondoids are present in virtually every petroleum (oils and gas condensates) as well as oil source-rock extracts.[11] The natural concentration of diamondoids in petroleum varies by orders of magnitude. For instance, methyldiamantane concentrations in relatively low-maturity crude oils from the central valley of California, are on the order of a few parts per million (ppm). Low-maturity oils sourced from the Jurassic-age Smackover Formation, Gulf Coast, USA, have methyldiamantane concentrations of 20–30 ppm. Deeply-buried petroleums such as gas condensate from deep formation, which have undergone substantial cracking as a result of intense heat, may have methyldiamantane concentration in the thousands of ppms.

The high diamondoid concentrations of some gas condensates and other feedstocks occur because of the high thermal stability of diamondoids compared to the other petroleum components. These diamondoids may be remnants of petroleum degradation by a geologic process over time and temperature conditions where other hydrocarbons were thermally cracked or reduced to gas and pyrobitumen. Because of this natural concentrating mechanism, in some gas condensates, diamondoids may become the dominant species. In addition, because they are extremely stable molecules, diamondoids survive and become concentrated in certain refinery streams after processing, e.g., cracking, hydrocracking, etc. The art has come to refer to adamantane, diamantane, triamantane and substituted analogs thereof as "lower diamondoids". Tetramantane and larger diamondoids and substituted analogs are referred as "higher diamondoids". That nomenclature is used herein. The lower diamondoid components show no isomers or chirality and are readily synthesized, distinguishing them from "higher diamondoids".

Among other properties, diamondoids have by far the most thermodynamically stable structures of all possible hydrocarbons that possess their molecular formulas due to the fact that diamondoids have the same internal "crystalline lattice" structure as diamonds. It is well established that diamonds exhibit extremely high tensile strength, extremely low chemical reactivity, electrical resistivity greater than aluminum trioxide ($Al_2O_3$) and excellent thermal conductivity.

In addition, tetramantane and other higher diamondoids have sizes in the nanometer range and, in view of the properties noted above, the inventors contemplate that such compounds would have utility in micro- and molecular-electronics and nanotechnology applications. In particular, the rigidity, strength, stability, thermal conductivity, variety of structural forms and multiple attachment sites shown by these higher diamondoid molecules makes possible accurate construction of robust, durable, precision devices with nanometer dimensions. It has been estimated that Micro-ElectroMechanical Systems (MEMs) constructed out of diamond should last 10,000 times longer then current polysilicon MEMs, and diamond is chemically benign and would not promote allergic reactions in biomedical applications.[2] The higher diamondoids would have similar attractive properties. Furthermore, some of the many isomers of the higher diamondoids possess chirality, offering opportunities for making nanotechnology objects of great structural specificity and ones which have useful optical properties. Applications of these higher diamondoids include molecular electronics, photonics, nanomechanical devices, and nanostructured polymers and other materials.

Notwithstanding the advantages of tetramantane and other higher diamondoids, the art fails to readily provide for compositions comprising these higher diamondoids.

For example, while Lin, et al.[3] report the natural occurrence of tetramantane, pentamantane and hexamantane in deep petroleum reservoirs. However, they were only able to identify such compounds in ionized form as part of a mass spectroscopy analysis.

Likewise, while Chen, et al.[4] discloses methods for isolation of high purity lower diamondoid fractions and components, the disclosed methods provide for distilling a diamondoid-comprising feedstock into 5 overhead components. These overhead components include unsubstituted adamantane, substituted adamantane, unsubstituted diamantane, substituted diamantane, and unsubstituted triamantane. Chen, et al. further recite that the pot material recovered after said distillation comprises a major amount of substituted triamantane and minor amounts of tetramantane and pentamantane. There was, however, no disclosure in Chen, et al. of the relative amounts of tetramantane and pentamantane in the pot material and Table 3 of Chen indicates only the presence of triamantane and tetramantane in the pot material and no attempt to isolare any high diamondoid is reported.

Other efforts to recover diamondoid fractions from naturally-occurring hydrocarbonaceous feedstocks have dealt with recovering the lower diamondoids illustrated by adamantane, diamantane and triamantane and various side-chain-containing analogues thereof primarily for the purpose of recovering these components from a natural gas stream in order to prevent operational problems in natural gas productions due to precipitation of these components in the production equipment. See, for example, the four related patents to Alexander, et al.[5-8] One or more of these patents disclose: 1) extracting lower diamondoids from a gas stream with a solvent and further extraction by sorption on silica gel; 2) extracting lower diamondoids by use of a heat exchanger; 3) extracting lower diamondoids from a gas stream using a porous solid such as zeolite. Recovery of lower diamondoids from a gas stream is also disclosed by Swanson[9] and recovery of lower diamondoids from a liquid stream is disclosed by Partridge, et al. 10

While synthetic routes to prepare diamondoids have provided for all of the lower diamondoids (adamantane through triamantane) by carbocation-mediated, thermo-dynamically controlled super-acid equilibration, this synthetic route, when applied to the synthesis of tetramantane and other higher diamondoids is blocked by severe kinetic (mechanistic) constraints. All attempts to synthesize the higher diamondoids by this thermodynamic equilibration route have proven futile. McKervey, et al.[12] have reported, however, the synthesis in low yields (e.g.,~10%) of anti-tetramantane from 1,6-dicarboxyl diamanatane using in the final step of the synthesis a gas-phase rearrangement over a platinum catalyst at 360° C. As is apparent, the use of such a starting material coupled with its low availability renders this synthetic procedure commercially unattractive and, moreover, it does not provide for the synthesis of other tetramantanes or other higher diamondoids.

In view of the above, there is an ongoing need in the art to provide for compositions comprising tetramantane and other higher diamondoids thereof. In view of the synthetic difficulties, there is also a need in the art to develop processes for recovering tetramantane and other higher diamondoids from natural sources.

SUMMARY OF THE INVENTION

This invention is directed to novel processes for providing compositions enriched in tetramantane and higher diamondoids from a hydrocarbonaceous feedstock comprising recoverable amounts of these higher diamondoid components.

In a first aspect, the processes of this invention entail removing at least a portion of the components from the feedstock having a boiling point lower than the lowest boiling point higher diamondoid component selected for recovery and subsequently pyrolytically treating the feedstock under conditions wherein recoverable amounts of the selected higher diamondoid component or components are retained in the pyrolytically-treated feedstock. Accordingly, in this first aspect, this invention is directed to a process which comprises:

a) selecting a feedstock comprising recoverable amounts of a higher diamondoid component or components selected for recovery;

b) removing a sufficient amount of components from the feedstock having a boiling point less than the lowest boiling point higher diamondoid component selected for recovery under conditions wherein recoverable amounts of the higher diamondoid component or components selected for recovery are retained in the treated feedstock which is recovered; and c) thermally treating the treated feedstock recovered in b) above to pyrolyze at least a sufficient amount of non-diamondoid components therefrom to permit recovery of the selected higher diamondoid component or components from the pyrolytically-treated feedstock wherein the pyrolysis is conducted under conditions to provide for a thermally treated feedstock retaining recoverable amounts of the selected higher diamondoid component or components.

In common hydrocarbonaceous feedstocks, components having a boiling point less than the lowest boiling selected higher diamondoid component typically include non-diamondoid components as well as lower diamondoid components. Accordingly, in another of its process aspects, this invention is directed to a process for recovering a composition enriched in one or more selected higher diamondoid components which process comprises:

a) selecting a feedstock comprising recoverable amounts of a selected higher diamondoid component or components, non-diamondoid components having a boiling point both below and above the lowest boiling point selected higher diamondoid component, and at least one lower diamondoid component;

b) removing a sufficient amount of non-diamondoid components having a boiling point below the lowest boiling point selected higher diamondoid component as well as lower diamondoid components from the feedstock under conditions to provide a treated feedstock wherein the selected higher diamondoid component or components are retained therein; and c) thermally treating said treated feedstock recovered in b) to pyrolyze at least a sufficient amount of non-diamondoid components therefrom to permit recovery of the selected higher diamondoid components from the pyrolytically-treated feedstock.

The order of the procedures for removal of the lower boiling point components and the pyrolysis of the feedstock are interchangeable. Accordingly, a further aspect of this invention is directed to a process for recovering a composition enriched in a selected higher diamondoid component or components which process comprises:

a) selecting a feedstock comprising recoverable amounts of a selected higher diamondoid component or components;

b) thermally treating the feedstock to pyrolyze at least a sufficient amount of non-diamondoid components therefrom to permit recovery of the selected higher diamondoid component or components from the pyrolytically-treated feedstock wherein said pyrolysis is conducted under conditions to provide for a treated feedstock retaining recoverable amounts of the selected higher diamondoid componenet or components; and c) removing a sufficient amount of those components from the feedstock surviving pyrolysis which components have a boiling point less than the lowest boiling point selected higher diamondoid component under conditions wherein recoverable amounts of the selected higher diamondoid component or components are retained in the treated feedstock.

It is understood, however, that due to their thermal stability, the components surviving pyrolysis which have a boiling point less than the lowest boiling selected higher diamondoid component will include at least a portion of the lower diamondoids originally present in the feedstock. Accordingly, still a further aspect of this invention is directed to a process for recovering a composition enriched in a selected higher diamondoid component or components which process comprises:

a) selecting a feedstock comprising recoverable amounts of a selected higher diamondoid component or components, non-diamondoid components, and at least one lower diamondoid component;

b) thermally treating said feedstock to pyrolyze at least a portion of the non-diamondoid components under conditions wherein recoverable amounts of the selected higher diamondoid component or components are retained in said pyrolytically treated feedstock; and c) removing a sufficient amount of lower diamondoid components from the pyrolytically treated feedstock under conditions to provide a treated feedstock from which the selected higher diamondoid component or components can be recovered.

It will be appreciated that in all of these aspects of the invention, it is possible, and often likely, that the higher diamondoid-containing feedstocks will contain several higher diamondoid components some of which are to be selected and some of which are not to be selected. Depending upon which of these higher diamondoid components are present and which of these are selected, it is possible that there will be nonselected higher diamondoids having a boiling point below the lowest boiling point of the lowest boiling point selected higher diamondoids. These lower boiling nonselected higher diamondoids may be removed, at least partially, with the other lower boiling components, such as the lower diamondoids.

When employing feedstocks sufficiently free of non-diamondoid materials, recovery of tetramantane components and pentamantane components do not always require thermal pyrolysis to effect their recovery. When thermal pyrolysis is not employed, after removal of the lower diamondoid components, the tetramantane components and pentamantane components can be recovered from the treated feedstock by separation techniques disclosed herein. Accordingly, in another of its process aspects, this invention is directed to a process for recovering a composition enriched in tetramantane and pentamantane components which process comprises:

a) selecting a feedstock comprising recoverable amounts of tetramantane and pentamantane components and at least one lower diamondoid component and;

b) removing a sufficient amount of the lower diamondoid components from the feedstock under conditions to provide a treated feedstock from which tetramantane and pentamantane components can be recovered; and c) recovering tetramantane and pentamantane components from said treated feedstock by separation techniques selected from the group consisting of chromatographic techniques, thermal diffusion techniques, zone refining, progressive recrystalization and size separation techniques.

In a preferred embodiment for each of the above processes, the feedstock employed therein comprises at least about 1 ppb (more preferably at least about 25 ppb and still more preferably at least about 100 ppb of selected higher diamondoid components.

In another preferred embodiment for each of the above processes, sufficient amounts of lower diamondoid components are removed from the feedstock to provide a ratio of lower diamondoid components (triamantane components and lower) to higher diamondoid components (tetramantane components and higher) of no greater than 9:1; more preferably, a ratio of no greater than 2:1; and even more preferably, a ratio of no greater than 1:1.

In still another preferred embodiment for each of the above processes, after removal of the lower diamondoid components from the feedstock, at least about 10%, more preferably at least 50% and still more preferably at least 90% of said [tetramantane components and] higher diamondoids components are retained in the feedstock as compared to that amount found in the feedstock prior to the removal.

In yet another preferred embodiment, after pyrolysis of the feedstock, at least about 10%, more preferably at least about 50%, and still more preferably at least about 90% of said [tetramantane components and] higher diamondoid components are retained in the feedstock after pyrolytic treatment compared to that amount found in the feedstock prior to pyrolytic treatment.

Preferably, the recovered feedstock produced by the above processes is further purified by chromatography, membrane size separation, crystallization, sublimation and the like.

In one of its product aspects, this invention provides for a composition comprising at least tetramantane and pentamantane components wherein said composition comprises at least about 10 weight percent tetramantane components and at least about 0.5 weight percent pentamantane components based on the total weight of the diamondoids in the composition.

In yet another preferred embodiment, this invention provides for a composition comprising at least tetramantane and pentamantane components wherein said composition comprises at least about 25 weight percent tetramantane components, still more preferably at least about 50 weight percent tetramantane components, and at least about 0.5 weight percent pentamantane components based on the total weight of the diamondoids in the composition.

Preferably, this composition further comprises hexamantane and higher components. More preferably, the hexamantane components found in any such composition do not include the fully condensed cyclohexamantane of the formula $C_{26}H_{30}$ and having a molecular weight of 342.

In still another of its product aspects, this invention provides for a preferred composition comprising at least tetramantane and pentamantane components wherein said composition comprises at least about 10 weight percent tetramantane components and at least about 0.5 weight percent pentamantane components based on the total weight of the composition. More preferably, such compositions comprise at least about 25 weight percent tetramantane components, and still more preferably at least about 50 weight percent tetramantane components, and at least about 0.5 weight percent pentamantane components based on the total weight of the composition.

Preferably, this composition further comprises hexamantane and higher diamondoid components.

BRIEF DESCRIPTION OF THE DRAWINGS

In FIG. 9, the GC/MS total ion current chromatogram illustrates the presence of higher diamondoids at levels allowing isolation. In FIG. 10, the GC/MS ion chromatogram (m/z 394) illustrates the presence of the isomeric heptamantanes. In FIG. 11, the GC/MS total ion chromatogram (TIC) illustrates the presence of heptamantanes at levels allowing isolation.

FIG. 30 is a table depicting the number of different molecular weights in each higher diamondoid series and the value of those molecular weights.

FIG. 31 is a distillation chart illustrating distillation cuts on a higher diamondoid-containing feedstock selected to favor the enrichment of selected various higher diamondoids.

FIGS. 32 and 33 are charts illustrating elution sequences for a variety of individual higher diamondoids on two different chromatography columns: ODS and Hypercarb.

DETAILED DESCRIPTION OF THE INVENTION

Figure 1:
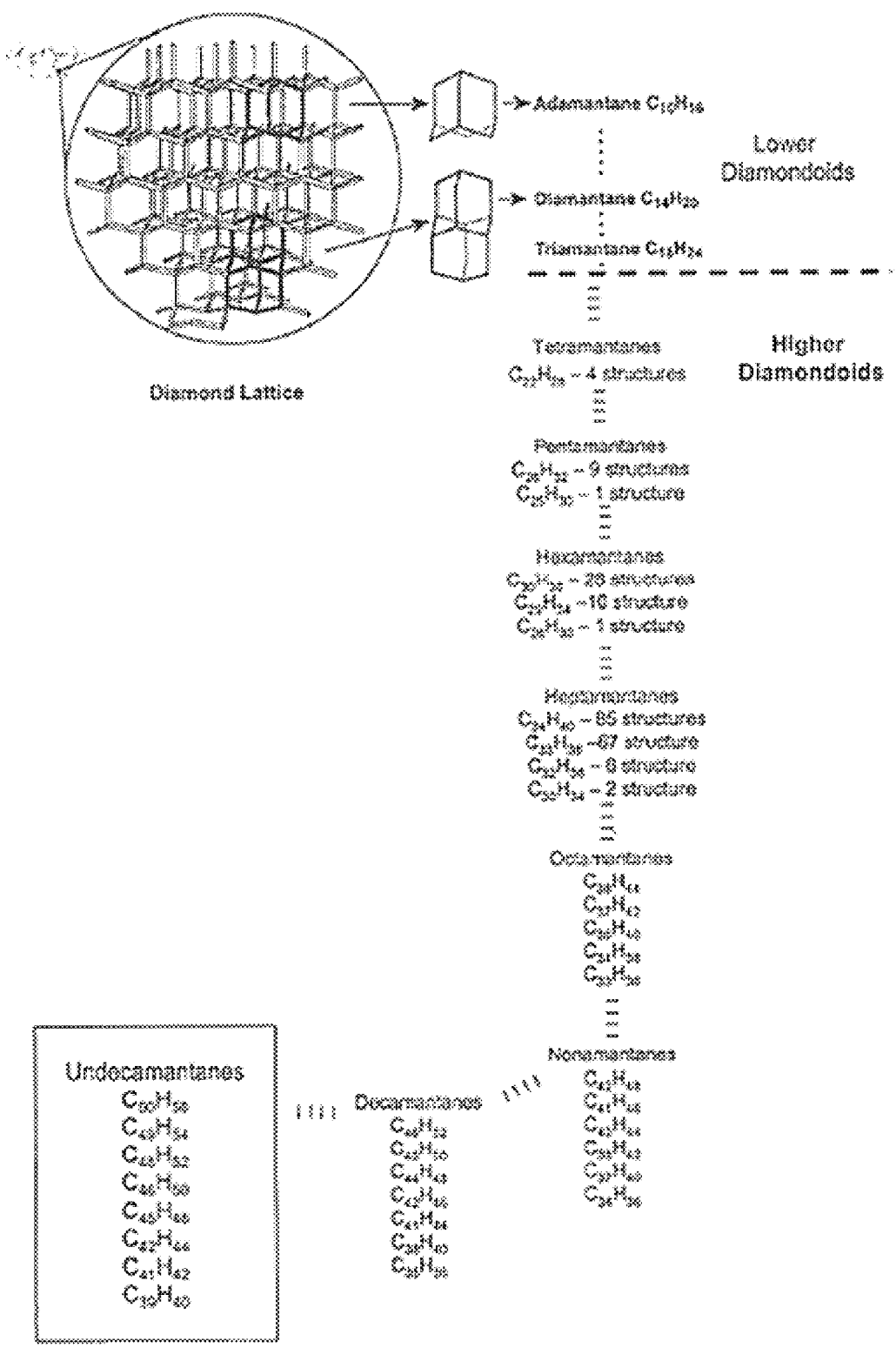
FIG. 1 illustrates the cage-shaped structure of diamondoids and their correlation to diamonds. Specifically, illustrated is the correlation of the structures of diamondoids to subunits of the diamond crystal lattice.

This invention is directed to processes for the recovery and purification of higher diamondoid components from hydrocarbonaceous feedstocks as well as compositions comprising such higher diamondoids. However, prior to describing this invention in further detail, the following terms will first be defined.

As used herein, the following terms have the following meanings.

The term "diamondoid" refers to substituted and unsubstituted caged compounds of the adamantane series including adamantane, diamantane, triamantane, tetramantane, pentamantane, hexamantane, heptamantane, octamantane, nonamantane, decamantane, undecamantane, and the like and also including all isomers and stereoisomers thereof. Substituted diamondoids preferably comprise from 1 to 10 and more preferably 1 to 4 alkyl substituents.

The term "lower diamondoid components" or "adamantane, diamantane and triamantane components" refers to any and/or all unsubstituted and substituted derivatives of adamantane, diamantane and triamantane.

The term "higher diamondoid components" refersto any and/or all substituted and unsubstituted diamondoids corresponding to tetramantane and above including tetramantane, pentamantane, hexamantane, heptamantane, octamantane, nonamantane, decamantane, undecamantane, and the like including all isomers and stereoisomers thereof. Preferably, the higher diamondoids include substituted and unsubstituted tetramantane, pentamantane, hexamantane, heptamantane, octamantane, nonamantane, decamantane and undecamantane. FIG. 30 is a Table which shows representative higher diamondoids together with their molecular weights.

The term "tetramantane components" refer to any and/or all substituted and unsubstituted diamondoids corresponding to tetramantane.

The term "pentamantane components" refer to any and/or all substituted and unsubstituted diamondoids corresponding to pentamantane. The term "non-ionized diamondoid components" refers to higher diamondoid components which do not carry a charge such as a positive charge generated during mass spectral analysis wherein the phrase "higher diamondoid components" is as defined herein.

The term "non-ionized tetramantane components" refers to tetramantane components which do not carry a charge such as a positive charge generated during mass spectral analysis.

The term "non-ionized pentamantane components and diamondoid components higher than pentamantane" refers to pentamantane components and higher diamondoid components larger than pentamantane which do not carry a charge such as a positive charge generated during mass spectral analysis.

The terms "selected higher diamondoid components" and the like refers to that one or more substituted or unsubstituted higher diamondoids that are desired to be isolated or "enriched" in a product.

The terms "nonselected higher diamondoid components" and the like refer to those higher diamondoids that are not "selected higher diamondoids".

The term "enriched" when used to describe the state of purity of one or more higher diamondoid components refers to such materials at least partially separated from the feedback, and in the case of "enriched" individual higher diamondoid components, concentrated at least 25 and preferably at least 100 times the original concentration exhibited in the feedstock. Preferably "enriched" higher diamondoid or "enriched" higher diamondoid components make up at least 25%, especially at least 50% (i.e., 50–100%), more preferably at least 75% and yet more preferably at least 95% or even at least 99% by weight of the overall material in which they are present or in other words exhibit a weight purity of at least 25%, 50%, 75%–95% or 99% of such material.

The term "feedstock" or "hydrocarbonaceous feedstock" refers to hydro-carbonaceous materials comprising recoverable amounts of higher diamondoids. Preferably, such feedstocks include oil, gas condensates, refinery streams, oils derived from reservoir rocks, oil shale, tar sands, and source rocks, and the like. Such components typically, but not necessarily, comprise one or more lower diamondoid components as well as non-diamondoid components. The latter is typically characterized as comprising components having a boiling point both below and above the lowest boiling point tetramantane which boils at about 350° C. at atmospheric pressure. Typical feedstocks may also contain impurities such as sediment, metals including nickel, vanadium and other inorganics. They may also contain heteromolecules containing sulfur, nitrogen and the like. All of these nondiamondoid materials are included in "nondiamondoid components" as that term as defined herein.

The term "nonselected materials" refers to the collection of feedstock components that are not "selected higher diamondoids" and include "nondiamondoid components", "lower diamondoids" and "nonselected higher diamondoid" as these terms are defined herein.

The term "remove" or "removing" refers to processes for removal of non-diamondoid components and/or lower diamondoid components and/or nonselected higher diamondoid components from the feedstock. Such processes include, by way of example only, size separation techniques, distillation, evaporation either under normal or reduced pressure, well head separators, sorption, chromatography, chemical extraction, crystallization and the like. For example, Chen, et al.[4] disclose distillation processes for removing adamantane, substituted adamantane, diamantane, substituted diamantane, and triamantane from a hydrocarbonaceous feedstock. Size separation techniques include membrane separations, molecular sieves, gel permeation, size exclusion chromatography and the like.

The terms "distillation" or "distilling" refers to atmospheric, reduced pressure distillation, and elevated pressure distillation processes on the hydrocarbonaceous feedstock which are conducted under conditions wherein the distillation is terminated when a portion and, preferably, at least 50 weight percent of adamantane, diamantane and triamantane components is removed from the feedstock. Unless otherwise specified, distillation temperatures are reported as atmospheric equivalents.

The terms "fractionation" and "fractionating" refer to processes in which materials in a mixture of materials are separated from each other such as by differential solubility, differential vapor pressure, differential chromatographic affinity and the like.

The terms "thermal treating to pyrolysis" and the like refer to either atmospheric, reduced pressure or elevated pressure heating of the feedstock or a feedstock fraction to pyrolyze a portion of one or more components in the feedstock.

The term "non-diamondoid components of a feedstock" refers to components of the feedstock or a feedstock fraction which are not diamondoid in character wherein the term "diamondoid" is as defined herein.

The term "retained" refers to retention of at least a portion of the higher diamondoid components found in the recovered feedstock when compared to the amount of such diamondoids found in the original feedstock. In a preferred embodiment, at least about 10 weight percent of the higher diamondoid components are retained in the recovered feedstock; more preferably, at least about 50 weight percent of the higher diamondoid components are retained in the recovered feedstock; and still more preferably, at least about 90 weight percent of the higher diamondoid components are retained in the recovered feedstock; each based on the total amount of such diamondoids found in the feedstock prior to treatment.

The term "chromatography" refers to any of a number of well known chromatographic techniques including, by way of example only, column or gravity chromatography (either normal or reverse phase), gas chromatography, high performance liquid chromatography, and the like.

The term "alkyl" refers to straight and branched chain saturated aliphatic groups typically having from 1 to 20 carbon atoms, more preferably 1 to 6 atoms ("lower alkyls"), as well as cyclic saturated aliphatic groups typically having from 3 to 20 carbon atoms and preferably from 3 to 6 carbon atoms ("lower alkyls" as well). The terms "alkyl" and "lower alkyl" are exemplified by groups such as methyl, ethyl, propyl, butyl, isopropyl, isobutyl, sec-butyl, t-butyl, n-heptyl, octyl, cyclopropyl, cyclobutyl, cyclopentyl, cyclohexyl and the like.

Methodology

The processes of this invention can be conducted with readily available feedstocks using the following general methods and procedures. It will be appreciated that where typical or preferred process conditions (i.e., reaction temperatures, times, solvents, pressures, etc.) are given, other process conditions can also be used unless otherwise stated. Optimum reaction conditions may vary with feedstocks, but such conditions can be determined by one skilled in the art by routine optimization procedures.

Furthermore, the higher diamondoids of this invention will typically contain one or more isomers or stereoisomers and substituted diamondoids will typically contain one or more chiral centers. Accordingly, if desired, such compounds can be prepared or isolated as pure isomers or stereoisomers, e.g., as individual enantiomers or diastereomers, or as stereoisomer-enriched mixtures. All such isomers and stereoisomers (and enriched mixtures) are included within the scope of this invention, unless otherwise indicated. Pure stereoisomers (or enriched mixtures) may be prepared using, for example, crystallizations, optically active solvent or stereoselective reagents well-known in the art. Alternatively, racemic mixtures of such compounds can be separated using, for example, chiral column chromatography, chiral resolving agents and the like.

In the processes of this invention, a feedstock is selected such that said feedstock comprises recoverable amounts of one or more selected higher diamondoid components. Preferably, such feedstock comprises at least about 1 ppb of one or more higher diamondoid components, more preferably, at least about 25 ppb and still more preferably at least about 100 ppb. It is understood, of course, that feedstocks having higher concentrations of higher diamondoid components facilitate recovery of these components.

Preferred feedstocks include, for example, natural gas condensates and refinery streams having high concentrations of higher diamondoids. With regard to the latter, such refinery streams include hydrocarbonaceous streams recoverable from cracking processes, distillations, coking and the like. Particularly preferred feedstocks include gas condensates feedstocks recovered from the Norphlet Formation in the Gulf of Mexico and from the LeDuc Formation in Canada.

In one embodiment, the feedstocks used in the processes of this invention typically comprise non-diamondoid components having a boiling point both below and above the lowest boiling point higher diamondoid component selected for recovery as well as one or more lower diamondoid components. These feedstocks will usually contain a mixture of higher diamondoids. Depending upon which higher diamondoids are selected, some of these higher diamondoids may have boiling points below the selected diamondoid's boiling point. Typically, the lowest boiling point higher diamondoid component selected for recovery will have a boiling point of greater than about 335° C. In typical feedstocks, the concentration of lower diamondoids to higher diamondoids is generally about 260:1 or higher.

Figure 20:
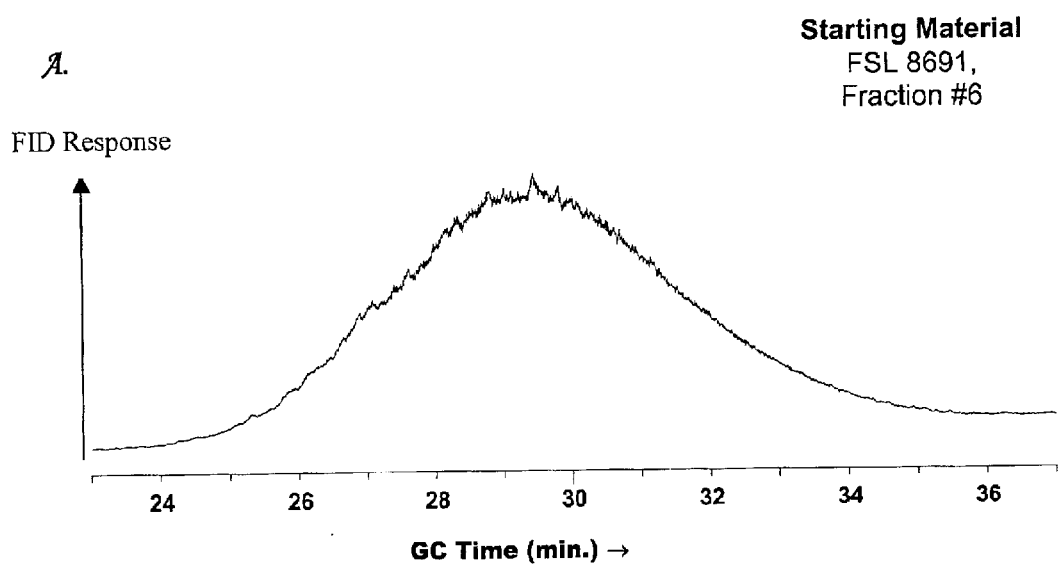
FIG. 20 illustrates a gas chromatogram (FID) of the distillate fraction #6 (Table 3B) of Feedstock B 650° F.+distillation bottoms, and the resulting product of pyrolytic processing this feedstock, showing the non-diamondoid components have been degraded and pentamantanes, hexamantanes and highly condensed heptamantanes components that have become available for isolation.
Figure 20:
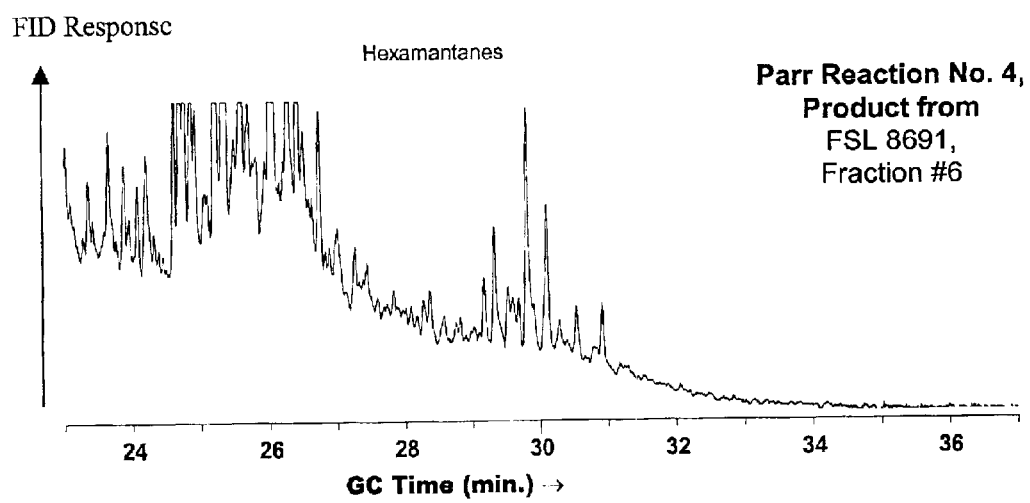
Figure 21:
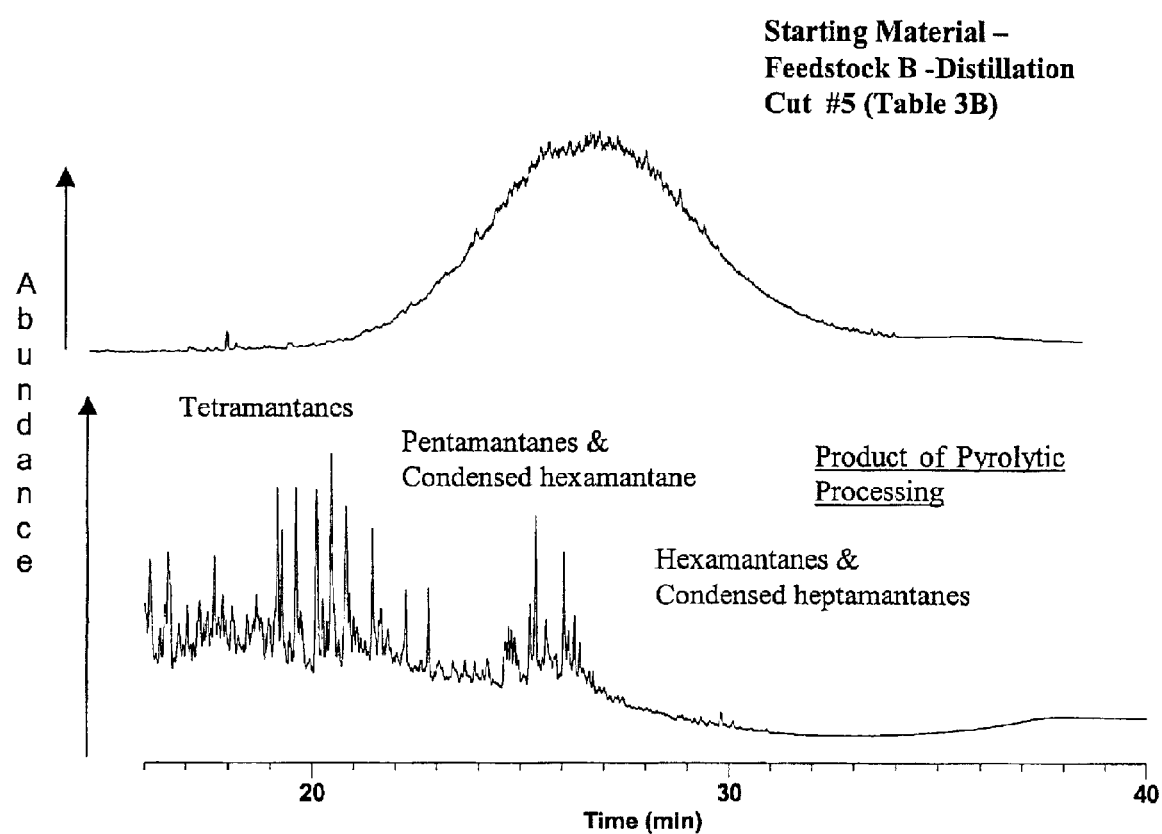
FIG. 21 illustrates a gas chromatogram (FID) of distillate fraction #5 (Table 3B) of Feedstock B 650° F.+distillation bottoms, and the resulting product of pyrolytic processing showing non-diamondoid components have been destroyed and tetramantanes, pentamantanes, hexamantanes and highly condensed heptamantanes that have become available for isolation.

Moreover, as illustrated in FIGS. 20 and 21, typical feedstocks comprising higher diamondoid components also comprise non-diamondoid components.

In such feedstocks, selected higher diamondoid components often cannot be effectively recovered directly from the feedstock because of their low concentrations relative to the nonselected components. Accordingly, the processes of this invention may entail removal of a sufficient amount of these contaminants from the feedstock under conditions to provide a treated feedstock from which the selected higher diamondoid components can be recovered.

In one embodiment, the removal of contaminants includes distillation of the feedstock to remove non-diamondoid components as well as lower diamondoid components and in some cases other nonselected higher diamondoids having boiling points less than that of the lowest boiling point higher diamondoid component selected for recovery.

In a particularly preferred embodiment, the feedstock is distilled to provide cuts above and below about 335° C., atmospheric equivalent boiling point and, more preferably, above and below about 345° C. atmospheric equivalent boiling point. In either instance, the lower cuts, which are enriched in lower diamondoids and low boiling point non-diamondoid components are taken overhead and discarded and the higher boiling cut, which is enriched in higher diamondoids, is retained. It is understood, of course, that the temperature for the cut point during distillation is a function of pressure and that the above temperatures are atmospheric equivalents. A reduced pressure will result in a lower distillation temperature to achieve the same cut point whereas an elevated pressure will result in a higher distillation temperature to achieve the same cut point. The correlation of pressure/temperature from atmospheric distillation to either reduced pressure or elevated pressure distillation is well within the skill of the art.

Distillation can be operated to fractionate the feedstocks and provide several cuts in a temperature range of interest to provide the initial enrichment of the selected higher diamondoids or groups of selected higher diamondoids. The cuts, which are enriched in selected one or more diamondoids or a particular diamondoid component of interest, are retained and may require further purification. The following Table illustrates representative fractionation points that may be used to enrich various higher diamondoids in overheads. In practice it may be advantageous to make wider temperature range cuts which would often contain groups of higher diamondoids which could be separated in subsequent separation steps.

It shall be understood that substituted higher diamondoids may accordingly shift these preferred temperatures to higher temperatures due to the addition of substituent groups. Additional temperature refinements will allow for higher purity cuts for the diamondoid of interest. FIG. 31 provides further illustrations of how fractionation can provide cuts enriched in individual or multiple higher diamondoid components.

It will be further understood that fractionation can be stopped before a selected higher diamondoid is taken overhead. In this case the higher diamondoid can be isolated from the fractionation bottoms.

Other processes for the removal of lower diamondoids, unselected higher diamondoids, if any, and/or hydrocarbonaceous non-diamondoid components include, by way of example only, size separation techniques, evaporation either under normal or reduced pressure, crystallization, chromatography, well head separators, reduced pressure and the like. For example, lower diamondoids can be preferentially removed from feedstocks using a variety of techniques. First of all, adamantane and diamantane dissolved in deep gases, may crystallize during commercial gas and liquids production due to a drop in pressure. Commercially available well head separators effectively remove lower diamondoids from such feedstocks to avoid scaling problems in oil and gas production equipment. Other removal processes can utilize the larger sizes of the higher diamondoids to effect separation of lower diamondoids therefrom. For example, size separation techniques using membranes will allow a feedstock retained in the membrane to selectively pass lower diamondoids across the membrane barrier provided that the pore size of the membrane barrier is selected to differentiate between compounds having the size of higher diamondoid components as compared to lower diamondoid components. The pore size of molecular sieves such as zeolites and the like can also be used to effect size separation.

In a preferred embodiment, the removal process provides for a treated feedstock having a ratio of lower diamondoid components to higher diamondoid components of no greater than 9:1; more preferably, no greater than 2:1; and even more preferably, the ratio is no greater than 1:1. Even more preferably, after removal of the lower diamondoid component(s) from the feedstock, at least about 10%, more preferably at least 50% and still more preferably at least 90% of the higher diamondoid components are retained in the feedstock as compared to that amount found in the feedstock prior to the removal.

| | Fractionation Points | | | | | |
|---|---|---|---|---|---|---|
| | Most Preferred | | Preferred | | Useful | |
| Higher Diamondoid | Lower Cut Temperature (° C.) | Higher Cut Temperature (° C.) | Lower Cut Temperature (° C.) | Higher Cut Temperature (° C.) | Lower Cut Temperature (° C.) | Higher Cut Temperature (° C.) |
| Tetramantanes | 349 | 382 | 330 | 400 | 300 | 430 |
| Pentamantanes | 385 | 427 | 360 | 450 | 330 | 490 |
| Cyclohexamantanes | 393 | 466 | 365 | 500 | 330 | 550 |
| Hexamantanes | 393 | 466 | 365 | 500 | 330 | 550 |
| Heptamantanes | 432 | 504 | 395 | 540 | 350 | 600 |
| Octamantanes | 454 | 527 | 420 | 560 | 375 | 610 |
| Nonamantanes | 463 | 549 | 425 | 590 | 380 | 650 |
| Decamantanes | 472 | 571 | 435 | 610 | 390 | 660 |
| Undecamantanes | 499 | 588 | 455 | 625 | 400 | 675 |

When recovery of hexamantane and higher diamondoid components is desired, the feedstock will also be subjected to pyrolysis to effect removal of at least a portion of the hydrocarbonaceous non-diamondoid components from the feedstock. The pyrolysis effectively concentrates the amount of higher diamondoids in the pyrolytically treated feedstock thereby rendering their recovery possible.

Pyrolysis is effected by heating the feedstock under vacuum conditions or in an inert atmosphere, at a temperature of at least about 400° C. and, preferably, from about 400 to about 500° C., more preferably from about 400 to about 450° C., and especially 410 to 430° C.; for a period of time to effect pyrolysis of at least a portion of the non-diamondoid components of the feedstock. The specific conditions employed are selected such that recoverable amounts of [tetramantane components and] higher diamondoid components are retained in the feedstock. The selection of such conditions is well within the skill of the art.

Preferably, pyrolysis is continued for a sufficient period and at a sufficiently high temperature to thermally degrade at least about 10% of the non-diamondoid components (more preferably at least about 50% and even more preferably at least about 90%) from the pyrolytically treated feedstock based on the total weight of the non-diamondoid components in the feedstock prior to pyrolysis.

In yet another preferred embodiment, after pyrolysis of the feedstock, at least about 10%, more preferably at least about 50%, and still more preferably at least about 90% of the higher diamondoid components are retained in the feedstock after pyrolytic treatment compared to that amount found in the feedstock prior to pyrolytic treatment.

In a preferred embodiment, removal of lower diamondoids and low boiling point hydrocarbonaceous non-diamondoid components from the feedstock precedes pyrolytic treatment. However, it is understood, that the order of these procedures can be inverted such that pyrolysis occurs prior to removal of lower diamondoids from the feedstock.

The pyrolysis procedure, while a preferred embodiment, is not always necessary. This arises because the concentration of higher diamondoid can be sufficiently high in certain feedstocks that the treated feedstock (after removal of the lower diamondoid components) can be used directly in purification techniques such as chromatography, crystallization, etc. to provide higher diamondoid components. However, when the concentration or purity of higher diamondoid components in the feedstock is not at the level to effect such a recovery, then a pyrolytic step should be employed.

Even when pyrolysis is employed, it is preferred to further purify the recovered feedstock using one or more purification techniques such as chromatography, crystallization, thermal diffusion techniques, zone refining, progressive recrystalization, size separation and the like. In a particularly preferred process, the recovered feedstock is first subjected to a gravity column chromatography using silver nitrate impregnated silica gel followed by HPLC using two different columns at differing selectivities to isolate the target diamondoids; and crystallization to provide crystals of the highly concentrated target higher diamondoids. Where higher diamondoid concentrations are not high enough for crystallization to occur, further concentration by, for example, preparative capillary gas chromatography may be necessary.

Compositions

The above processes provide novel higher diamondoid compositions. For example, in one embodiment, these processes provide a composition comprising at least tetramantane and pentamantane components wherein said composition comprises at least about 10 weight percent tetramantane components and at least about 0.5 weight percent pentamantane components based on the total amount of diamondoid components present. Alternatively, the compositions of this invention comprise at least about 10 weight percent tetramantane components and at least about 0.5 weight percent pentamantane components based on the total weight of the composition.

In a preferred embodiment, the composition comprises at least tetramantane and pentamantane components wherein said composition comprises at least about 25 weight percent tetramantane components and at least 1 weight percent pentamantane components based on the total amount of diamondoid component present; and, even more preferably, at least about 50 weight percent tetramantane components and at least 1 weight percent pentamantane components based on the total amount of diamondoid component present.

In another preferred embodiment, the composition comprises at least tetramantane and pentamantane components wherein said composition comprises at least about 25 weight percent tetramantane components and at least 1 weight percent pentamantane components based on the total weight of the composition; and, even more preferably, at least about 50 weight percent tetramantane components and at least 1 weight percent pentamantane components based on the total weight of the composition.

In addition to the tetramantane and pentamantane components found in these compositions, the compositions preferably further comprise hexamantane components and, even more preferably, one or more of heptamantane, octamantane, nonamantane, decamantane, undecamantane components. More preferably, the hexamantane components found in any such composition do not include the fully condensed cyclohexamantane of the formula $C_{26}H_{30}$ and having a molecular weight of 342.

Further purification of these compositions will lead to compositions which comprise at least about 50% or more of tetramantane components (either as individual isomers or as a mixture of tetramantane isomers), pentamantane components (either as individual isomers or as a mixture of pentamantane isomers), hexamantane components (either as individual isomers or as a mixture of hexamantane isomers), heptamantane components (either as individual isomers or as a mixture of heptamantane isomers), octamantane components (either as individual isomers or as a mixture of octamantane isomers), nonamantane components (either as individual isomers or as a mixture of nonamantane isomers) decamantane components (either as individual isomers or as a mixture of decamantane isomers) and the like.

The compositions described above contain non-ionized higher diamondoid components.

Utility

The processes of this invention provide for compositions enhanced in higher diamondoids. These higher diamondoids are useful in micro- and molecular-electronics and nano-technology applications. In particular, the rigidity, strength, stability, thermal conductivity, variety of structural forms and multiple attachment sites shown by these molecules makes possible accurate construction of robust, durable, precision devices with nanometer dimensions.

In addition, these higher diamondoids can also be used in a high quality lubricating fluid which exhibits a high Viscosity Index and a very low pour point.[13] When so employed, these fluids comprise a fluid of lubricating viscosity and from about 0.1 to 10 weight percent diamondoids.

Still further, these higher diamondoids can be used as high density fuels in the manner described by Chung, et al.[14], incorporated herein by reference.

The following examples are offered to illustrate this invention and are not to be construed in any way as limiting the scope of this invention. Unless otherwise stated, all temperatures are in degrees Celsius.

As used herein and in the Figures, the following abbreviations have the following meanings. Any abbreviation not defined below has its generally accepted meaning.

| | | |
|---|---|---|
| API | = | American Petroleum Institute |
| ATM EQV | = | atmospheric equivalent |
| EOR Traps | = | end of run traps |
| FID | = | flame ionization detector |
| G | = | grams |
| GC | = | gas chromatography |
| GC/MS | = | gas chromatography/mass spectroscopy |
| HPLC | = | high performance liquid chromatography |
| HYD RDG | = | hydrometer reading |
| MIN | = | minute |
| ML | = | milliliters |
| ODS | = | octadecyl silane |
| pA | = | pico amps |
| ppb | = | parts per billion |
| RI | = | refractive index |
| SIM DIS | = | simulated distillation |
| ST | = | start |
| TIC | = | total ion current |
| VLT | = | vapor line temperature |
| VOL PCT | = | volume percent |
| WT PCT | = | weight percent |

EXAMPLES

Example 1

Isolation of Four Tetramantanes and One Pentamantane

The purpose of this example is to demonstrate procedures for the isolation of four tetramantane isomers and one pentamantane isomer using the methods of this invention. Since nondiamondoid components did not interfere with their isolation, these procedures did not employ a pyrolysis step. After removal of lower boiling point components (including some lower diamondoid components) from the feedstock by distillation, the tetramantane and pentamantane isomers in this example were recovered by chromatography and crystallization.

Step 1

Figure 2:
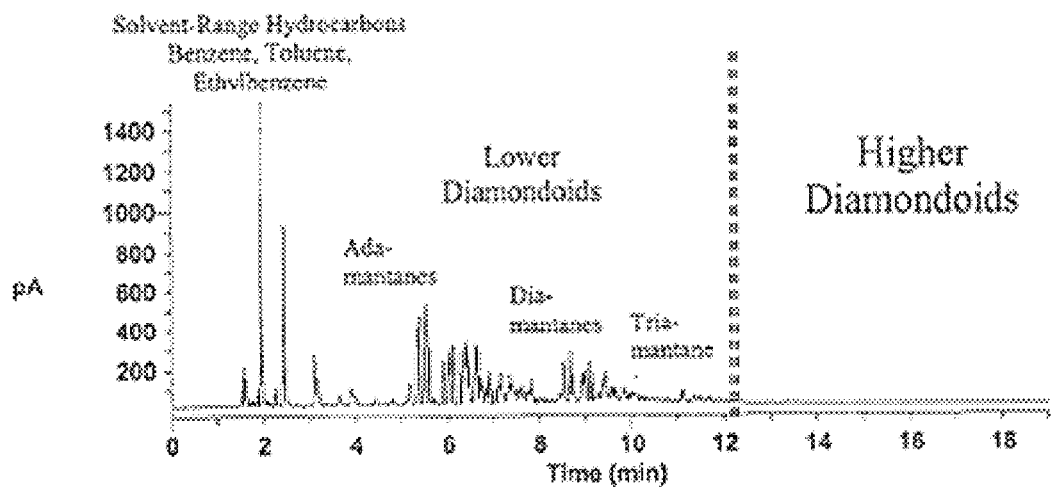
FIG. 2 illustrates the gas chromatogram of a gas condensate feedstock; one of the original feedstocks used in the Examples (Feedstock A).
Figure 3:
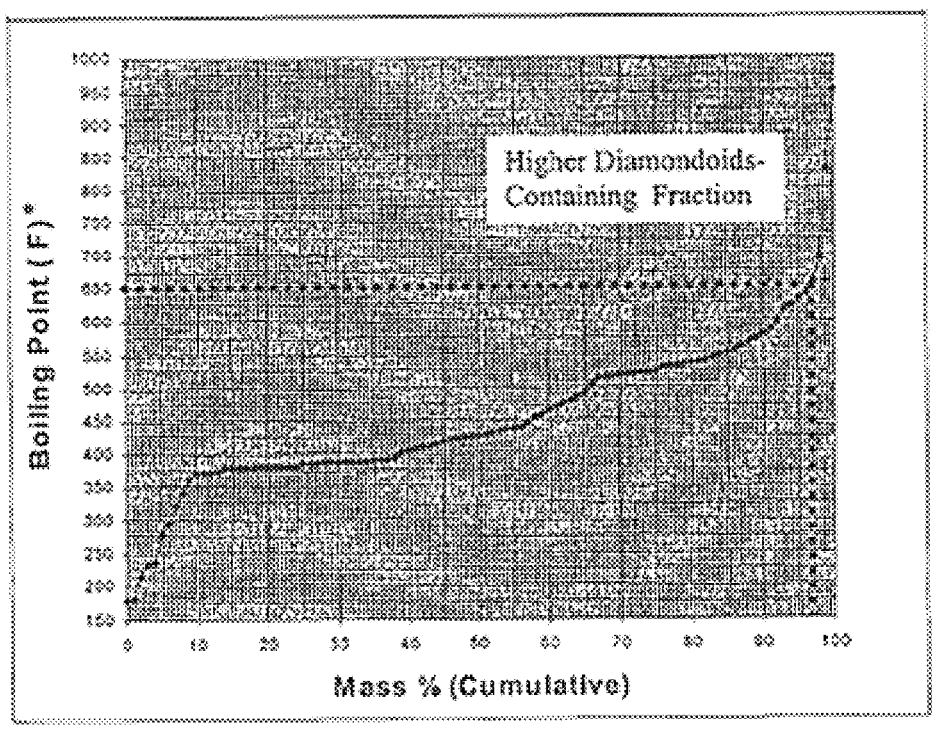
FIG. 3 illustrates a simulated distillation profile of a gas condensate feedstock containing petroleum byproducts used in the Examples (Feedstock B). Boiling points depicted are atmospheric equivalents.

Suitable starting materials were obtained. These materials included a gas condensate, Feedstock A (a gas chromatogram of this material is depicted in FIG. 2), and a gas condensate containing petroleum byproducts Feedstock B (a high temperature simulated distillation profile of this type of material is depicted in FIG. 3). Although other condensates, petroleums, or refinery cuts and product could have been used, these two materials were chosen due to their high diamondoid concentration, approximately 65 percent diamondoids and 0.3 weight percent higher diamondoids, as determined by GC and GC/MS. Both feedstocks were light colored and had API gravities between 19 and 20° API.

Step 2

Samples from Feedstocks A and B were distilled into a number of fractions based on boiling point to separate the lower boiling point components (non-diamondoids and lower diamondoids) and for further concentration and enrichment of particular diamondoids in various fractions. The yields of atmospheric distillate fractions of two separate samples of Feedstock B are shown in Table 1, below and are contrasted to the simulated distillation yields. As seen from Table 1, the simulation data is in agreement with the distillation data.

TABLE 1

Yields of Atmospheric Distillation Fractions from Two Separate Runs of Feedstock B

| Cut (° F.) | Sim Dis Est.'d Yields (Wt %) | Feedstock B (Run 2) Yields (Wt %) | Difference |
|---|---|---|---|
| To 349 | 8.0 | 7.6 | 0.4 |
| 349 to 491 | 57.0 | 57.7 | −0.7 |
| 491 to 643 | 31.0 | 30.6 | 0.4 |
| 643 and higher | 4.0 | 4.1 | −0.1 |

| Cut (° F.) | Sim Dis Est.'d Yields (Wt %) | Feedstock B (Run 1) Yields (Wt %) | Difference |
|---|---|---|---|
| To 477 | 63.2 | 59.3 | 3.9 |
| 477 to 515 | 4.8 | 7.3 | −2.5 |
| 515 to 649 | 28.5 | 31.2 | −2.7 |
| 649 and higher | 3.5 | 2.1 | 1.4 |

Figure 4:
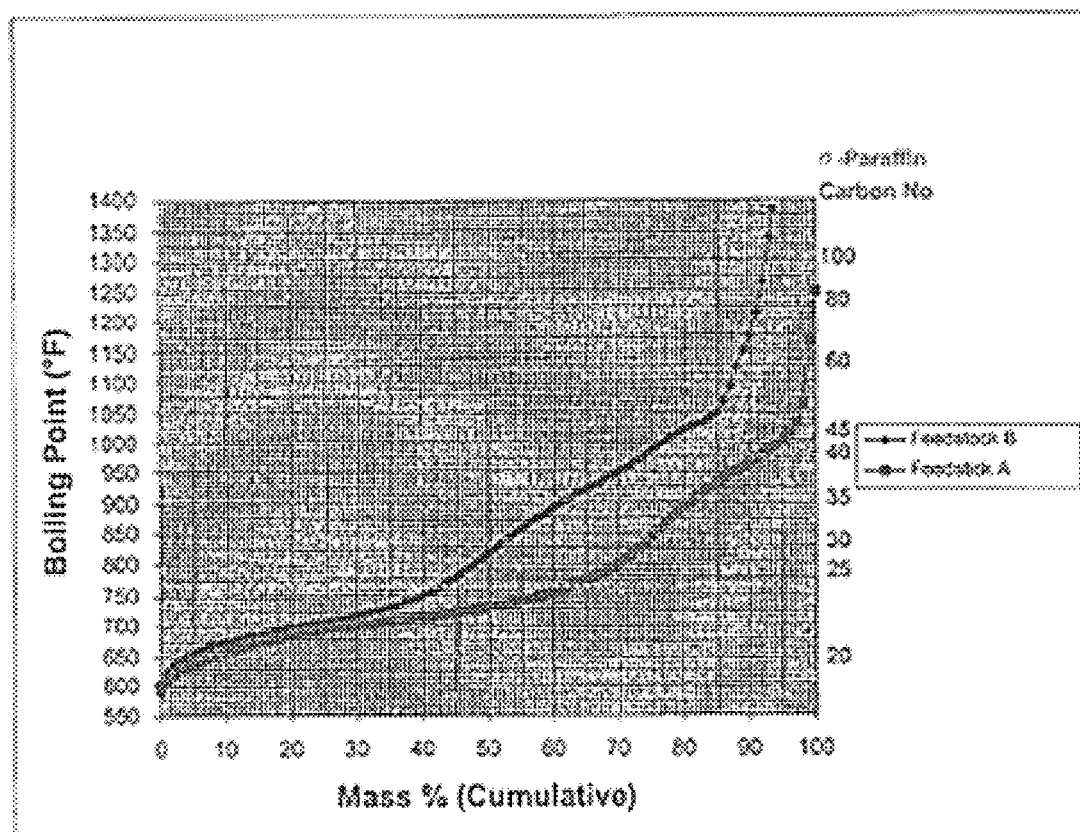
FIG. 4 illustrates a high temperature simulated distillation profile of atmospheric residue of diamondoid rich gas condensates; Feedstock A and Feedstock B. This Figure also illustrates the n-paraffin carbon number atmospheric equivalent boiling point.

Table 1 shows the yields for a simulated atmospheric distillation fractions from two separate runs of Feedstock B. FIG. 4 compares a high-temperature simulated distillation profile of the atmospheric residue of the gas condensates, Feedstock A and Feedstock B.

A sample of gas condensate, Feedstock A was distilled into 38 fractions to remove lower diamondoids and concentrate diamondoids of interest as verified by GC (see FIG. 5) wherein Fraction 33 was the recovered distillate, boiling in the range of from 675 to 750° F. and Fraction 38 was the recovered distillate, boiling in the range of from approximately 750 to 850° F. The temperature range for these fractions are atmospheric equivalent temperatures, wherein the actual distillation can occur under various conditions including reduced pressure.

Figure 12:
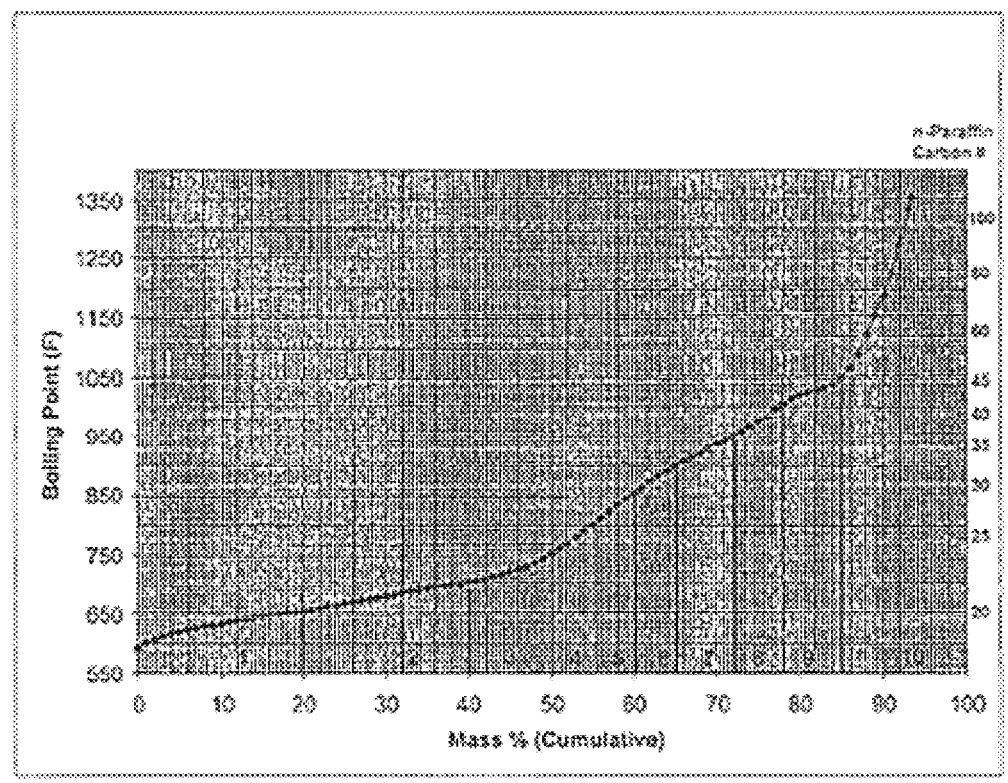
FIG. 12 illustrates a high temperature simulated distillation profile of Feedstock B using the atmospheric distillation 650° F.+bottoms as feedstock. This FIG. also illustrates the targeted cut points (1–10) for higher diamondoid isolations.

Additionally, Feedstock B was distilled into fractions containing higher diamondoids guided by high temperature simulated distillation curve (FIG. 12). The feed to the high temperature distillation process was the atmospheric 650° F.+bottoms. Complete Feedstock B distillation reports are given in Tables 2A&B. Tables 3A&B, illustrate the distillation reports for Feedstock B 650° F.+distillation bottoms.

TABLE 2A

Distillation Report for Feedstock B (FSL #8471)
Feedstock B
Column Used: Clean 9" × 1.4" Protruded Packed

| | VAPOR | DISTILLATION RECORD | | | | NORMALIZED | | ACTUAL | |
|---|---|---|---|---|---|---|---|---|---|
| CUT | TEMP ST-END | WEIGHT G | VOLUME ml @ 60° F. | API 60/60 | DENSITY @ 60 F. | WT PCT | VOL PCT | WT PCT | VOL PCT |
| 1 | 226 – 349 | 67.0 | 80 | 38.0 | 0.8348 | 7.61 | 8.54 | 7.39 | 8.26 |
| 2 | 349 – 491 | 507.7 | 554 | 22.8 | 0.9170 | 57.65 | 59.12 | 55.98 | 57.23 |
| 3 | 491 – 643 | 269.6 | 268 | 9.1 | 1.0064 | 30.62 | 28.60 | 29.73 | 27.69 |
| COL HOLDUP | | 0.2 | 0 | 6.6 | 1.0246 | 0.02 | 0.00 | 0.02 | 0.00 |
| BTMS | 643 + | 36.1 | 35 | 6.6 | 1.0246 | 4.09 | 3.74 | 3.98 | 3.62 |
| EOR TRAPS | | 0.0 | 0 | | | 0.00 | 0.00 | | 0.00 |
| TOTALS | | 880.6 | 937 | | | 100.00 | 100.00 | 97.09 | 96.80 |
| LOSS | | 26.4 | 31 | | | | | 2.91 | 3.20 |
| FEED | | 907.0 | 968 | 19.5 | 0.9371 | | | 100.00 | 100.00 |
| BACK CALCULATED API AND DENSITY | | | | 19.1 | 0.9396 | | | | |

TABLE 2B

Distillation Report for Feedstock B (FSL #8471)
Feedstock B
Column Used: Clean 9" × 1.4" Protruded Packed

TEMPERATURE DEGREES F — API GRAVITIES

VAPOR — OBSERVED

| VLT | ATM EQV. | POT | PRESSURE TORR | REFLUX RATIO | CUT NO | VOLUME ml @ 60° F. | WEIGHT G | HYD RDG | TEM P° F. | 60° F. |
|---|---|---|---|---|---|---|---|---|---|---|
| 93 | 225.8 | 262 | 50.000 | 3:1 | | START OVERHEAD | | | | |
| 198 | 349.1 | 277 | 50.000 | 3:1 | 1 | 80 | 67.0 | 39.6 | 80.0 | 38.0 |
| 321 | 490.8 | 376 | 50.000 | 3:1 | 2 | 554 | 507.7 | 24.1 | 80.0 | 22.8 |
| | | | Cut 2 looks Milky, White crystals form in Run Down Line. Heat Lamp applied to drip tube. | | | | | | | |
| | | | Cool to transfer btms to smaller flask. | | | | | | | |
| 208 | 437.7 | 323 | 10.000 | 3:1 | | START OVERHEAD | | | | |
| 378 | 643.3 | 550 | 10.000 | 3:1 | 3 | 268 | 269.6 | 9.9 | 75.0 | 9.1 |
| | | | Shutdown due to dry pot | | | | | | | |
| | | | END OF RUN TRAPS | | | 0 | 0.0 | | | |
| | | | VOLUME DISTILLED | | | 902 | | | | |
| | | | COLUMN HOLDUP | | | 0 | 0.2 | 0.0 | 0.0 | 6.6 |
| | | | BOTTOMS | | | 35 | 36.1 | 7.2 | 72.0 | 6.6 |
| | | | RECOVERED | | | 937 | 880.6 | | | |
| | | | FEED CHARGED | | | 968 | 907.0 | 20.7 | 80.0 | 19.5 |
| | | | LOSS | | | 31 | 26.4 | | | |

TABLE 3A

Vacuum Distillation Report for Feedstock B (FSL #8691)
Feedstock B-Atmospheric distillation resid 650° F. + bottoms
Column Used: Sarnia Hi Vac

TEMPERATURE DEGREES F — API GRAVITIES

VAPOR — VOLUME — OBSERVED

| VLT | ATM EQV. | POT | PRESSURE TORR | REFLUX RATIO | CUT NO | ml 60° F. | WEIGHT G | HYD RDG | TEMP ° F. | 60° F. |
|---|---|---|---|---|---|---|---|---|---|---|
| 315 | 601.4 | 350 | 5.000 | | | | START OVERHEAD | | | |
| 344 | 636.8 | 382 | 5.000 | | | 300 | READING | | | |

TABLE 3A-continued

Vacuum Distillation Report for Feedstock B (FSL #8691)
Feedstock B-Atmospheric distillation resid 650° F. + bottoms
Column Used: Sarnia Hi Vac

| TEMPERATURE DEGREES F | | | | | | | | API GRAVITIES | | |
|---|---|---|---|---|---|---|---|---|---|---|
| VAPOR | | | | | | VOLUME | | OBSERVED | | |
| VLT | ATM EQV. | POT | PRESSURE TORR | REFLUX RATIO | CUT NO | ml 60° F. | WEIGHT G | HYD RDG | TEMP ° F. | 60° F. |
| 342 | 644.9 | 389 | 4.000 | | | 500 | READING | | | |
| 344 | 656.3 | 395 | 3.300 | | 1 | 639 | 666.4 | 7.8 | 138.0 | 4.1 |
| 353 | 680.1 | 411 | 2.500 | | | 400 | READING | | | |
| 364 | 701.6 | 430 | 2.100 | | 2 | 646 | 666.9 | 9.4 | 138.0 | 5.6 |
| 333 | 736.0 | 419 | 0.400 | | | 200 | READING | | | |
| 336 | 751.9 | 432 | 0.300 | | 3 | 330 | 334.3 | 12.4 | 139.0 | 8.3 |
| 391 | 799.9 | 468 | 0.500 | | 4 | 173 | 167.7 | 19.0 | 139.0 | 14.5 |
| 411 | 851.6 | 500 | 0.270 | | 5 | 181 | 167.3 | 26.8 | 139.0 | 21.7 |
| 460 | 899.8 | 538 | 0.360 | | 6 | 181 | 167.1 | 27.0 | 139.0 | 21.9 |
| 484 | 950.3 | 569 | 0.222 | | 7 | 257 | 238.4 | 26.2 | 139.0 | 21.2 |
| Shut down distillation to check pot temperature limits with customer. (Drained trap material 5.3 grams) | | | | | | | | | | |
| 472 | 935.7 | 576 | 0.222 | | | | START OVERHEAD | | | |
| 521 | 976.3 | 595 | 0.340 | | 8 | 91 | 85.4 | 23.7 | 139.0 | 18.9 |
| 527 | 999.9 | 610 | 0.235 | | 9 | 85 | 80.8 | 23.0 | 139.0 | 18.2 |
| 527 | 1025.6 | 624 | 0.130 | | 10 | 98 | 93.8 | 21.6 | 139.0 | 16.9 |
| Drained remaining trap material of 16.5 grams (~4 grams of water) | | | | | | | | | | |
| | | MID AND | END OF RUN TRAPS | | | 20 | 17.8 | (mathematically combined) | | |
| | | | VOLUME DISTILLED | | | 2701 | | | | |
| | | | COLUMN HOLDUP | | | 4 | 4.0 | 0.0 | 0.0 | 3.4 |
| | | | BOTTOMS | | | 593 | 621.8 | 11.0 | 214.0 | 3.4 |
| | | | RECOVERED | | | 3298 | 3311.7 | | | |
| | | | FEED CHARGED | | | 3298 | 3326.3 | 18.0 | 234.0 | 8.6 |
| | | | LOSS | | | −5 | 14.6 | | | |

TABLE 3B

Distillation Report for Feedstock B-btms (FSL #8691)
Feedstock B-Atmospheric distillation resid 650° F. + bottoms
Column Used: Sarnia HiVac

| CUT | VAPOR TEMP ST-END | WEIGHT G | VOLUME ml @ 60° F. | API 60/60 | DENSITY 60° F. | WT PCT | VOL PCT | WT PCT | VOL PCT |
|---|---|---|---|---|---|---|---|---|---|
| 1 | 601 – 656 | 666.4 | 639 | 4.1 | 1.0435 | 20.12 | 19.38 | 20.03 | 19.40 |
| 2 | 656 – 702 | 666.9 | 646 | 5.6 | 1.0321 | 20.14 | 19.59 | 20.05 | 19.62 |
| 3 | 702 – 752 | 334.3 | 330 | 8.3 | 1.0122 | 10.09 | 10.01 | 10.05 | 10.02 |
| 4 | 752 – 800 | 167.7 | 173 | 14.5 | 0.9692 | 5.06 | 5.25 | 5.04 | 5.25 |
| 5 | 800 – 852 | 167.3 | 181 | 21.7 | 0.9236 | 5.05 | 5.49 | 5.03 | 5.50 |
| 6 | 852 – 900 | 167.1 | 181 | 21.9 | 0.9224 | 5.05 | 5.49 | 5.02 | 5.50 |
| 7 | 900 – 950 | 238.4 | 257 | 21.2 | 0.9267 | 7.25 | 7.79 | 7.17 | 7.80 |
| 8 | 950 – 976 | 85.4 | 91 | 18.9 | 0.9408 | 2.58 | 2.76 | 2.57 | 2.76 |
| 9 | 976 – 1000 | 80.8 | 85 | 18.2 | 0.9452 | 2.44 | 2.58 | 2.43 | 2.58 |
| 10 | 1000 – 1026 | 93.8 | 98 | 16.9 | 0.9535 | 2.83 | 2.97 | 2.82 | 2.98 |
| | COL HOLDUP | 4.0 | 4 | 3.4 | 1.0489 | 0.12 | 0.12 | 0.12 | 0.12 |
| BTMS | 1026 + | 621.8 | 593 | 3.4 | 1.0489 | 18.78 | 17.98 | 18.69 | 18.01 |
| | EOR TRAPS | 17.8 | 20 | | | 0.54 | 0.61 | 0.54 | 0.61 |
| | TOTALS | 3311.7 | 3298 | | | 100.00 | 100.00 | 99.56 | 100.15 |
| | LOSS | 14.6 | −5 | | | | | 0.44 | −0.15 |
| | FEED | 3326.3 | 3293 | 8.6 | 1.0100 | | | 100.00 | 100.00 |
| | BACK CALCULATED API & DENSITY | | | 9.4 | 1.0039 | | | | |

TABLE 4

Elemental Composition of Feedstock B
Analyses on Feedstock B 650 + F Resid

| Measured | Value |
|---|---|
| Nitrogen | 0.991 wt % |
| Sulfur | 0.863 wt % |
| Nickel | 8.61 ppm |
| Vanadium | <0.2 ppm |

Table 4 illustrates the elemental composition of Feedstock B atmospheric distillation (650° F.) residue including some of the identified impurities. Table 4 displays the weight percent nitrogen, sulfur, nickel and vanadium in Feedstock B. Subsequent steps remove these materials.

Step 3

Figure 5:
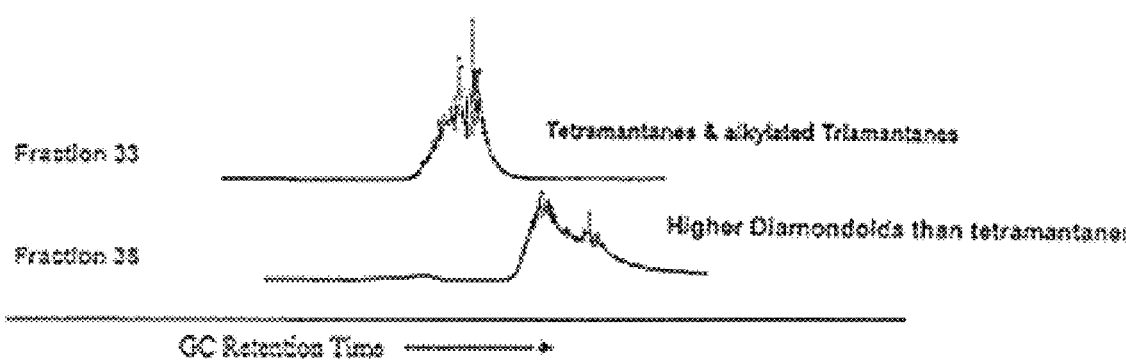
FIG. 5 illustrates gas chromatographic profiles of distillate fractions containing tetramantanes and higher diamondoids from a gas condensate, Feedstock A.

The higher diamondoids enriched following the separation of Step 2, were further isolated to a higher diamondoid fraction in the following way: in Feedstock A, a distillation fraction of interest for a particular higher diamondoid component (e.g., tetramantane—Fraction 33; a GC profile identifying this fraction is shown in FIG. 5) was passed through a silica-gel gravity chromatography column (using cyclohexane elution solvent) to remove polar compounds and asphaltenes. The use of a silver nitrate impregnated silica gel (10% wAgNO₃) provides cleaner diamondoid-containing fractions by removing the free aromatic and polar components. While it is not necessary to use this chromatographic aromatic separation method, it facilitates subsequent steps.

Step 4

The eluent from the column chromatography was analyzed by GC/MS to determine the approximate GC retention times of higher diamondoid species of interest, and each species was assigned a number representing their elution order of the GC/MS assay. These reference numbers are used to track individual higher diamondoid species in subsequent purification steps.

Step 5

Figure 6:
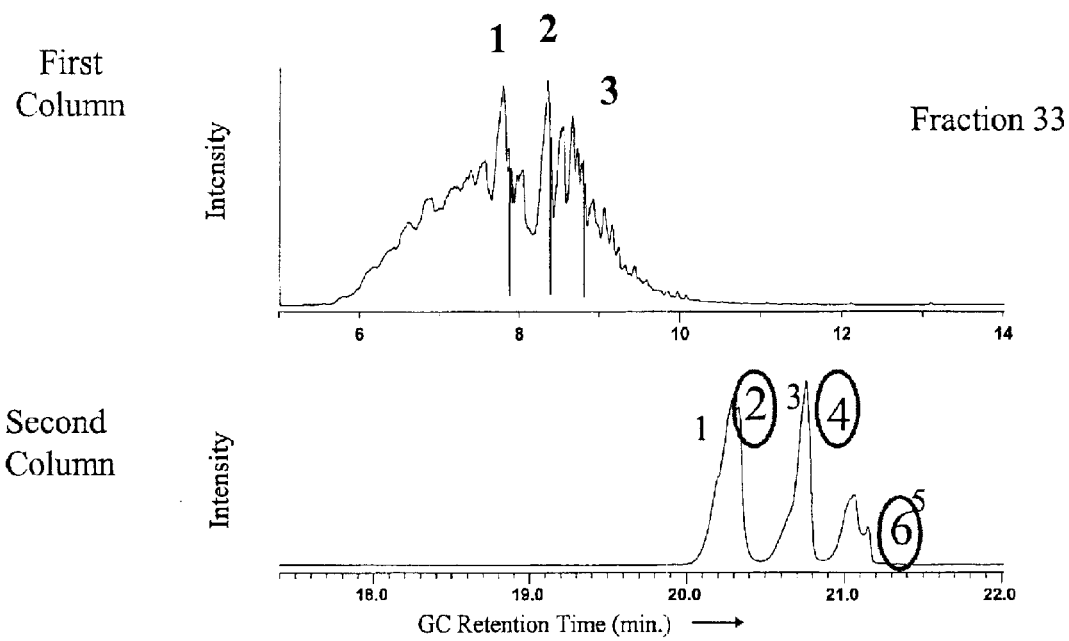
FIG. 6 illustrates the preparative capillary gas chromatographic data for tetramantane isolations. The first column shows cuts made on distillate fraction 33, Feedstock A. The bold face numbers refers to peaks of the tetramantanes. The second column shows peaks isolated and sent to the traps. The circled numbered peaks (2, 4, and 6) are the tetramantanes. It is noted that both enantiomers of the optically active tetramantane are contained within one of these peaks.

A two-column preparative capillary gas chromatograph was then used to isolate the target diamondoids from the distillate fractions cleaned-up by column chromatography. The results are shown in the top of FIG. 6, identified as cuts 1, 2 and 3. Using the retention times and patterns from GC/MS analysis (from step 4 above), the cut times for the target diamondoids (e.g., tetramantanes) were set for the first preparative capillary GC column, methyl silicone DB-1 equivalent.

The first column was used to concentrate the target diamondoids (e.g., tetramantanes) by taking cuts that were then sent to the second column (phenyl-methyl silicone, a DB-17 equivalent) (see the bottom of FIG. 6). The second column further separated and purified the target diamondoids and then sent them into individual vials (traps 1–6). GC trap fractions 2, 4 and 6 were collected and further processed.

Step 6

Figure 7:
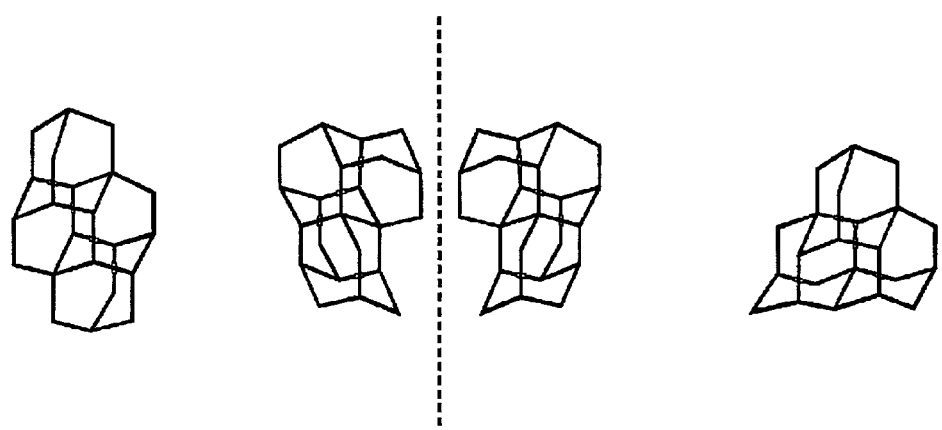
FIG. 7 illustrates the structures of the four-tetramantane isomers two of which are enantiomers.
Figure 8A:
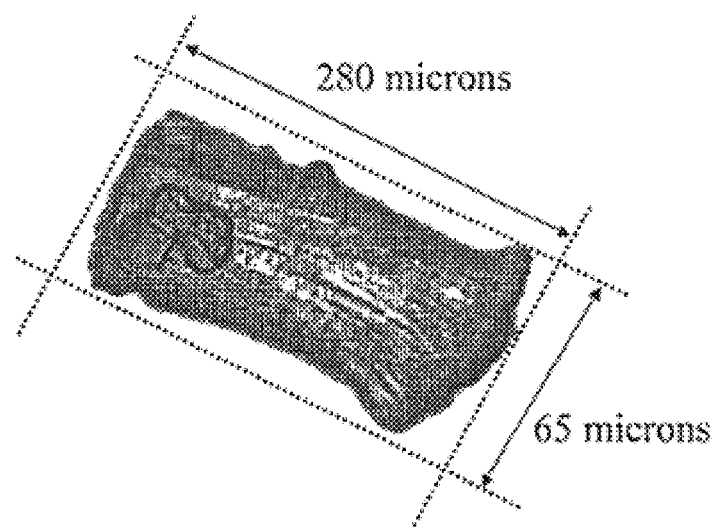
FIG. 8A was isolated from trap fraction 2, FIG. 8B was isolated from trap fraction 4, and FIG. 8C was isolated from trap fraction 6. Because the two enantiomeric tetramantanes have identical GC retentions times in FIG. 6, one of the crystals contains both enantiomers.
Figure 8B:
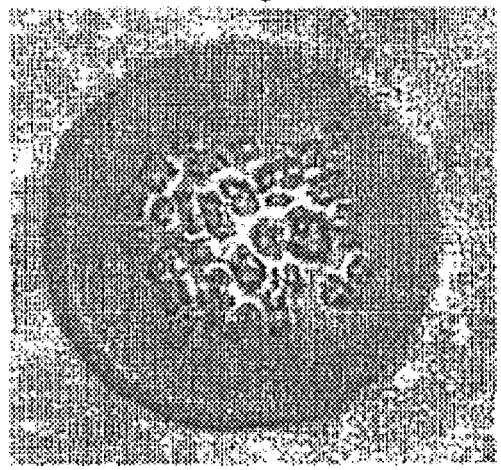
FIGS. 8(A, B, C) illustrates photomicrographs of tetramantane crystals isolated from Feedstock A by preparative gas chromatography (FIG. 6).
Figure 8C:
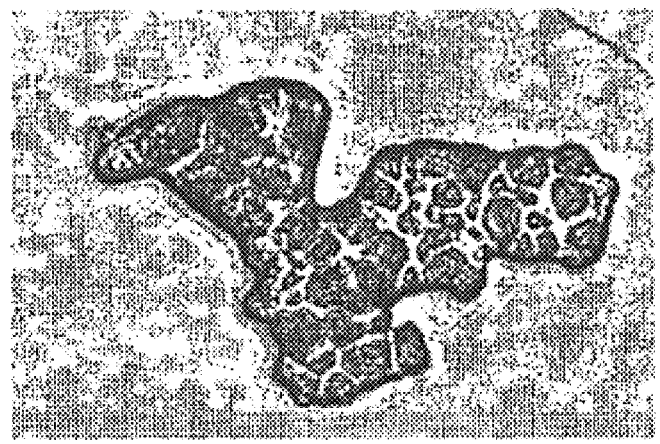

The highly concentrated diamondoids were then allowed to crystallize in the trap or from solution. Under the microscope at 30× magnification, crystals were visible in preparative GC trap fractions 2, 4, and 6 (see FIG. 6). Where concentrations were not high enough for crystallization to occur, further concentration by preparative GC was necessary. Structures of tetramantane isomers are shown in FIG. 7, including one, [123] tetramantane as two enantiomeric forms. FIGS. 8A, B and C illustrates photomicrographs of tetramantane crystals isolated from Feedstock A from preparative GC trap fraction #2, fraction #4 and fraction #6 respectively.

Step 7

After obtaining crystals of suitable size, material could be sent for structural determination using X-ray diffraction.

Figure 9:
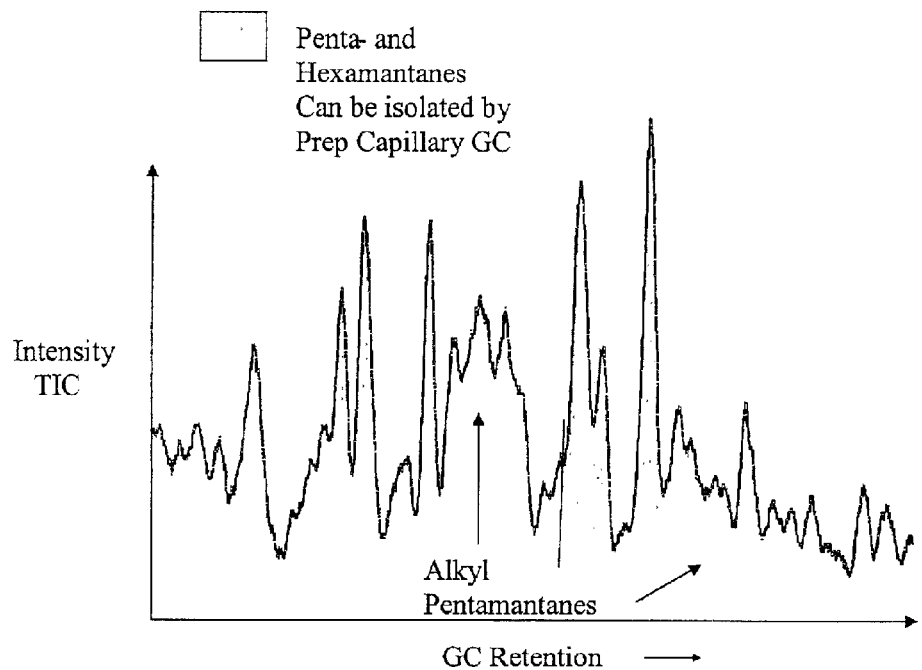
FIGS. 9–11 illustrate the GC retention time for a diamondoid condensate distilled and purified from Feedstock A, distillate fraction 38.
Figure 10:
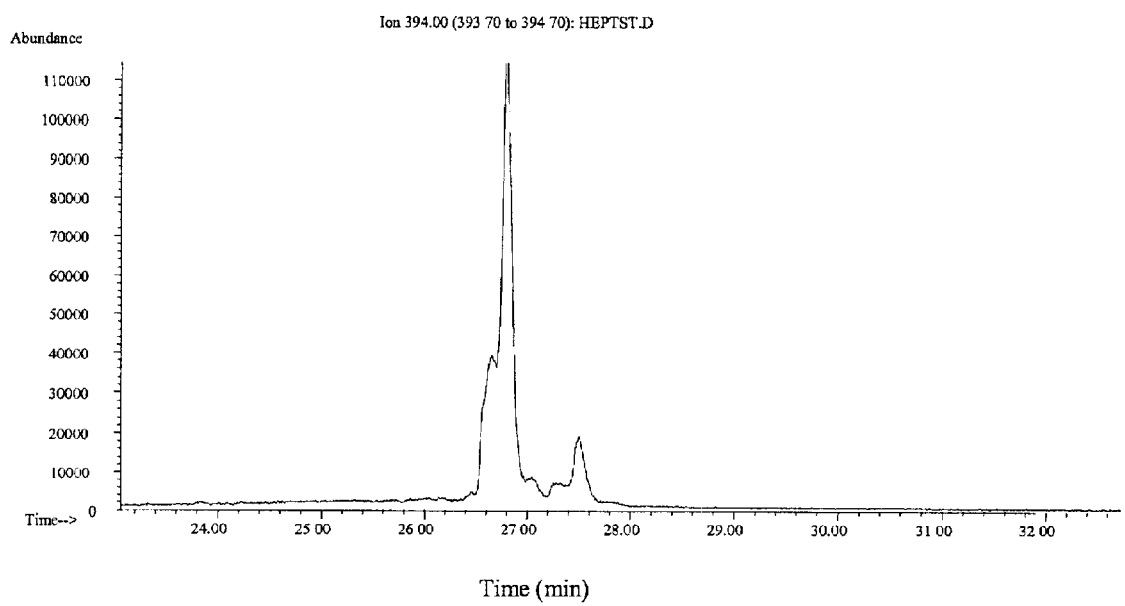
Figure 11:
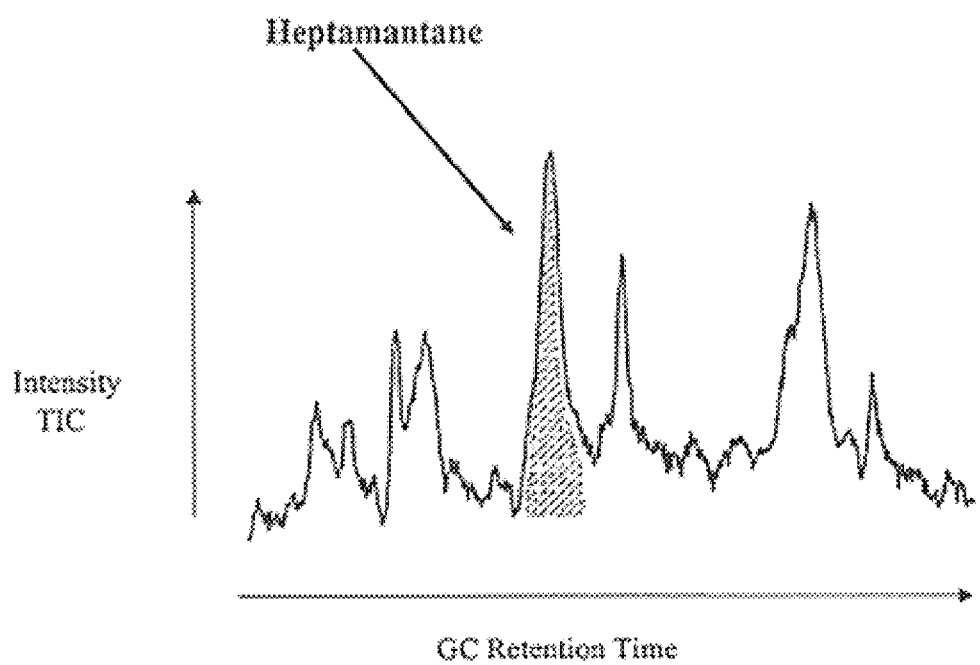

GC/MS (FIG. 9) showed the possible presence of target diamondoids higher than tetramantane (pentamantanes and hexamantanes) in distillate Fraction 38. Further GC/MS analyses of fraction 38 showed the presence of heptamantanes (FIGS. 10 and 11).

Example 2

Isolation of Tetramantanes Using Pyrolysis and HPLC

Figure 13:
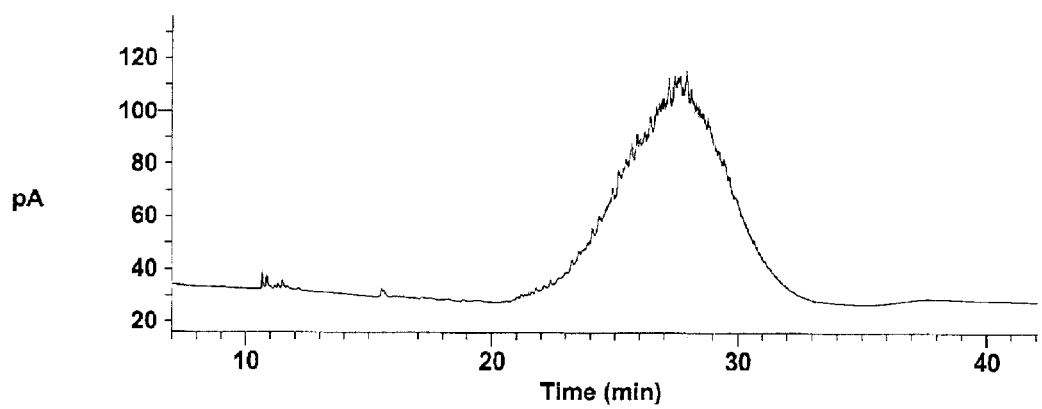
FIG. 13 illustrates the gas chromatogram of distillate Fraction #5 of Feedstock B atmospheric distillation 650° F.+bottoms illustrated in FIG. 12 and exemplified in Example 1.
Figure 14:
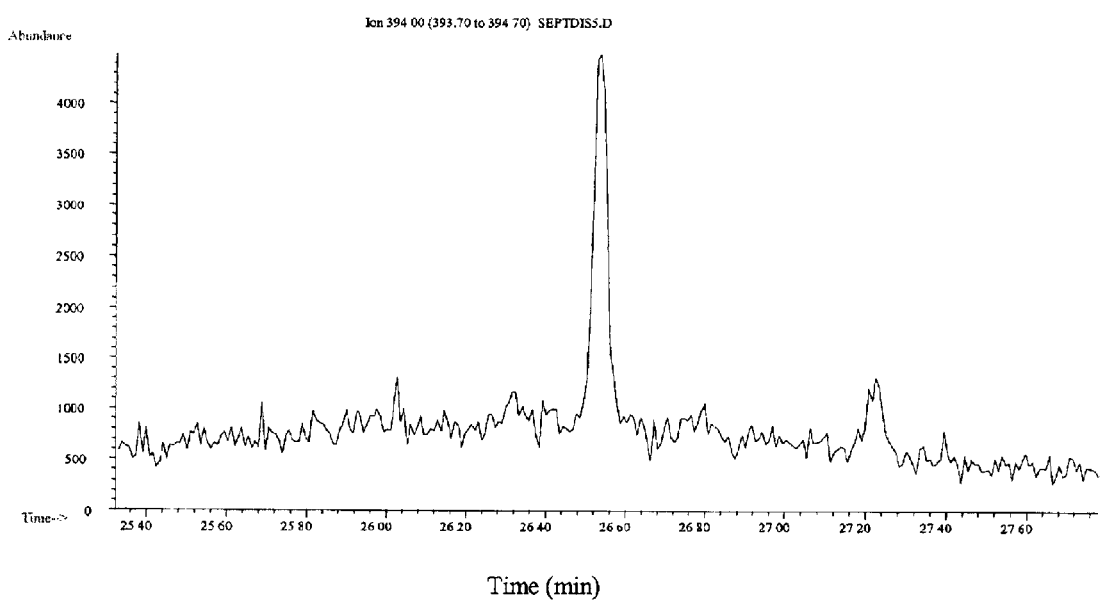
FIG. 14 illustrates the GC/MS selected ion chromatogram (m/z 394) showing the presence of the isomeric heptamantanes in the distillate Fraction #5 of Feedstock B atmospheric distillation 650° F.+bottoms.
Figure 32:
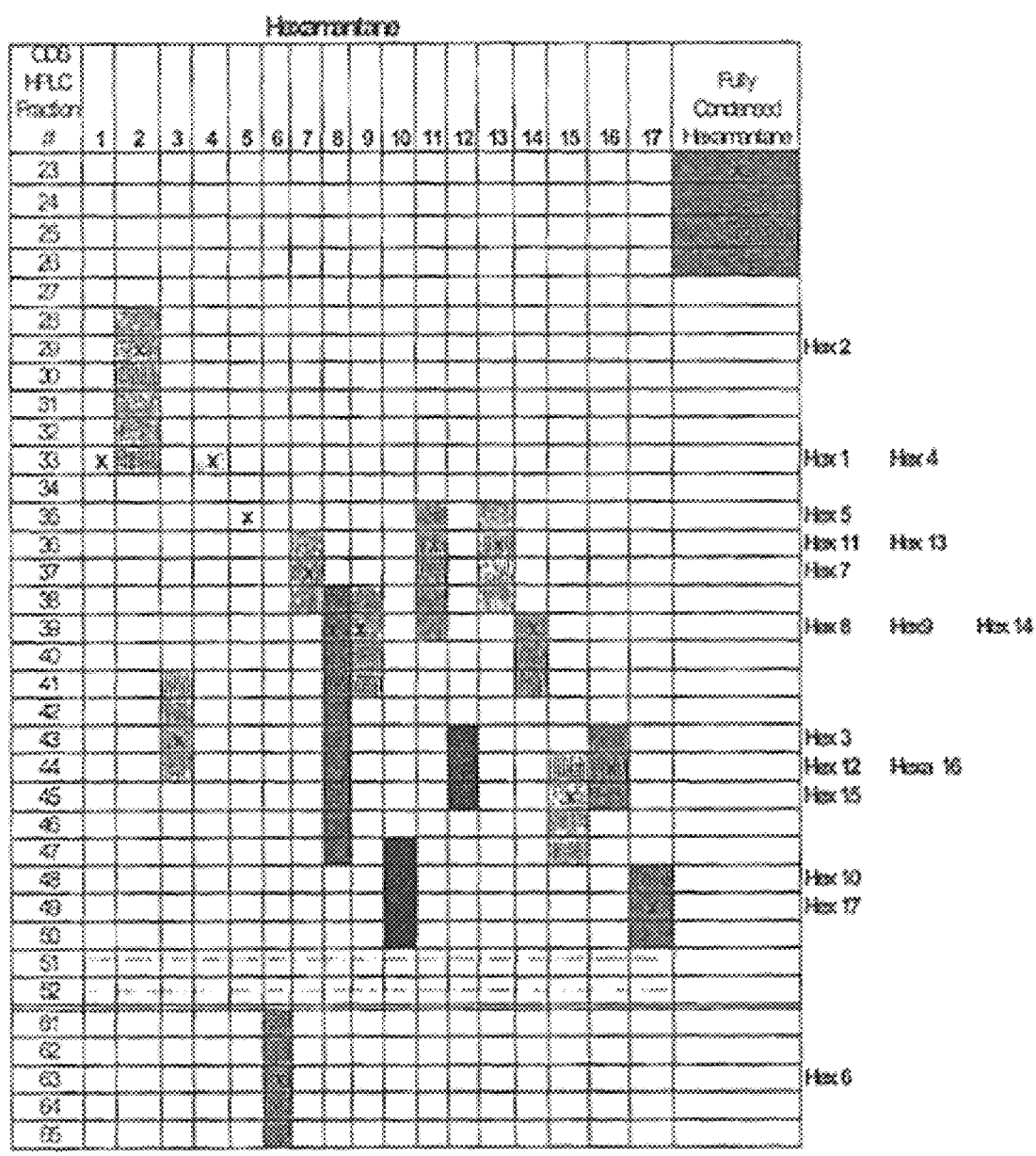

A method was developed to further purify distillate fractions such as distillate fraction #5 obtained from Feedstock B–Atmospheric distillation 650° F.+bottoms (Table 3A/B, FIG. 12 and FIG. 32) exploiting the great thermal stability of the higher diamondoid hydrocarbons relative to other crude oil components. FIG. 13 shows the GC profile of the distillate fraction #5 from Feedstock B–Atmospheric distillation 650° F.+bottoms (see FIG. 12 and Table 3A&B). The GC-MS ion chromatogram in FIG. 14 shows the presence of target heptamantanes in this distillate Fraction #5.

Removal of Non-diamondoids Using Pyrolysis

This method used a high-temperature reactor to pyrolyze and degrade a portion of the non-diamondoid components thereby enriching the diamondoids in the residue. FIGS. 15, 16, 20 and 21 illustrate this method and show gas chromatograms before pyrolysis (e.g. FIG. 15) and the resulting pyrolysis products (e.g. FIG. 16).

A PARR® reactor, from PARR INSTRUMENT COMPANY, Moline, Ill., was used to process the distillation column hold-up obtained after atmospheric distillation of a feedstream. For this example, Feedstock B 650° F.+distillation holdup was used as a feedstock for pyrolysis. Pyrolysis was then conducted on this sample by heating the sample under vacuum in a vessel at 450° C. for 20.4 hours.

Figure 15:
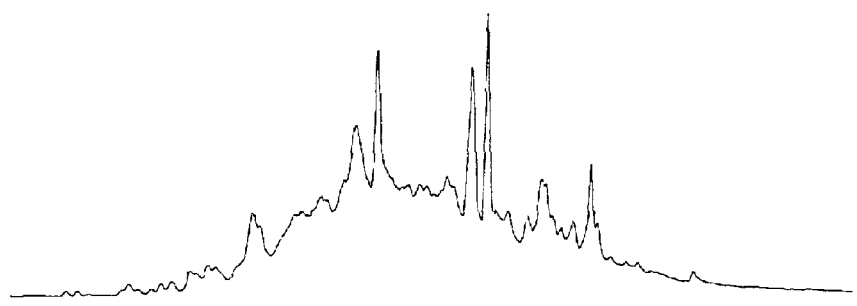
FIG. 15 illustrates the gas chromatogram of Feedstock B atmospheric distillation hold up fraction, exemplified in Example 1, which was used as feedstock in pyrolytic processing. The hold up fraction is the material recovered from the distillation column after distillation of Feedstock B at approximately 650° F.
Figure 16:
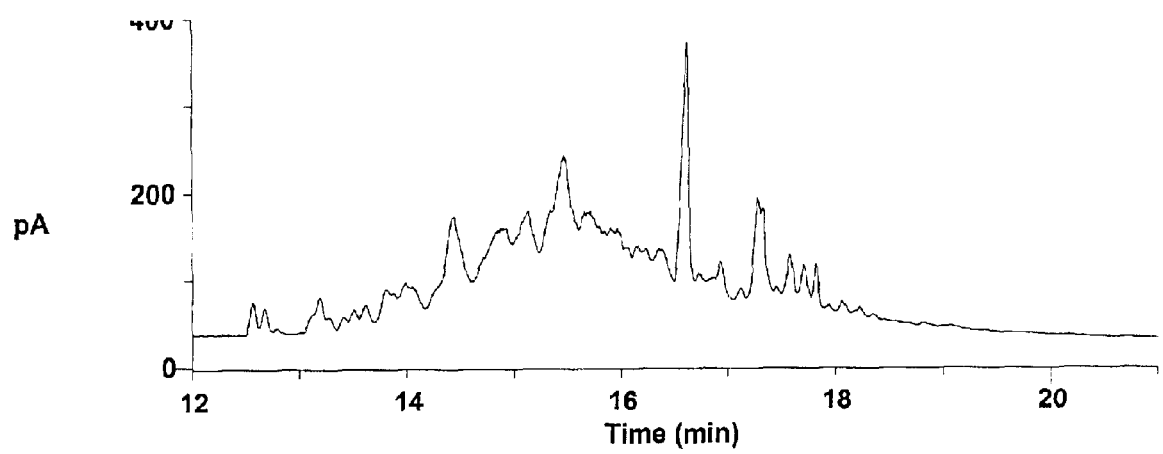
FIG. 16 illustrates the gas chromatogram of the pyrolytic product from the starting material in FIG. 15, i.e. the holdup fraction of Feedstock B atmospheric distillation 650° F.+bottoms, showing the degradation of non-diamondoid components.

FIG. 15 shows the gas chromatogram of the distillation holdup and FIG. 16 shows the chromatograph of the products of the pyrolytic process. A comparison of FIGS. 15 and 16 show that the pyrolysis process has removed major non-diamondoid components leaving a residue enriched in diamondoids.

Isolations of Diamondoids Using HPLC

Figure 17:
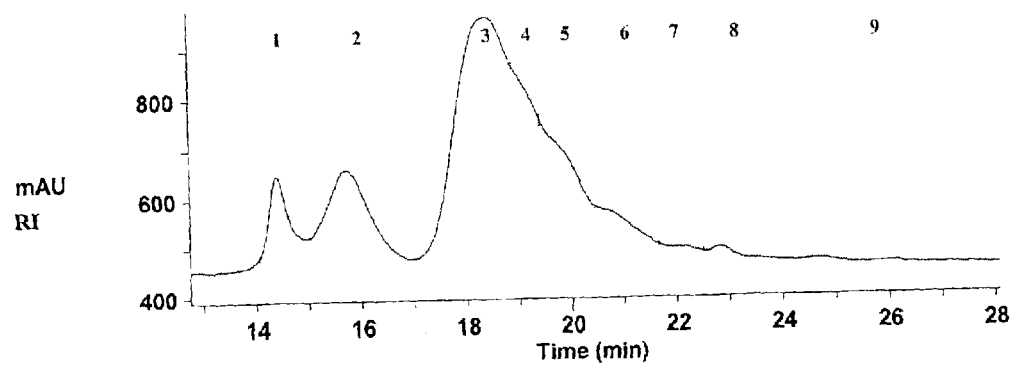
FIG. 17 illustrates the preparative ODS HPLC trace of Feedstock A gas condensate distillation fraction #32 showing fractions taken (1–9).

In addition to the pyrolysis method described above, HPLC was also shown to provide sufficient enrichments of some higher diamondoids to allow for their crystallization. In some cases, reverse-phase HPLC with acetone as mobile phase can be used to effect this purification. A preparative HPLC run of Feedstock A, gas condensate distillate Fraction #32 was performed and the HPLC chromatogram recorded using a differential refractometer is shown in FIG. 17. Nine fractions where taken during the run as marked on FIG. 17.

Figure 18:
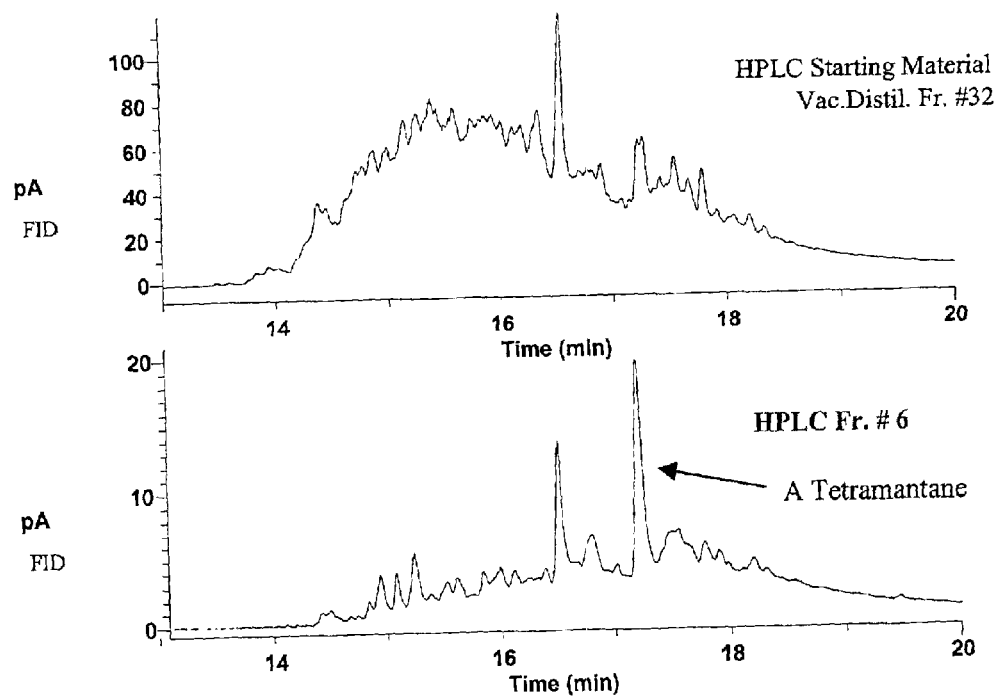
FIG. 18 illustrates gas chromatograms showing Feedstock A, distillate fraction #32, as compared to its HPLC fraction #6 indicated as shown in FIG. 17. HPLC fraction #6 shows significant enrichment in one of the tetramantane components.
Figure 19:
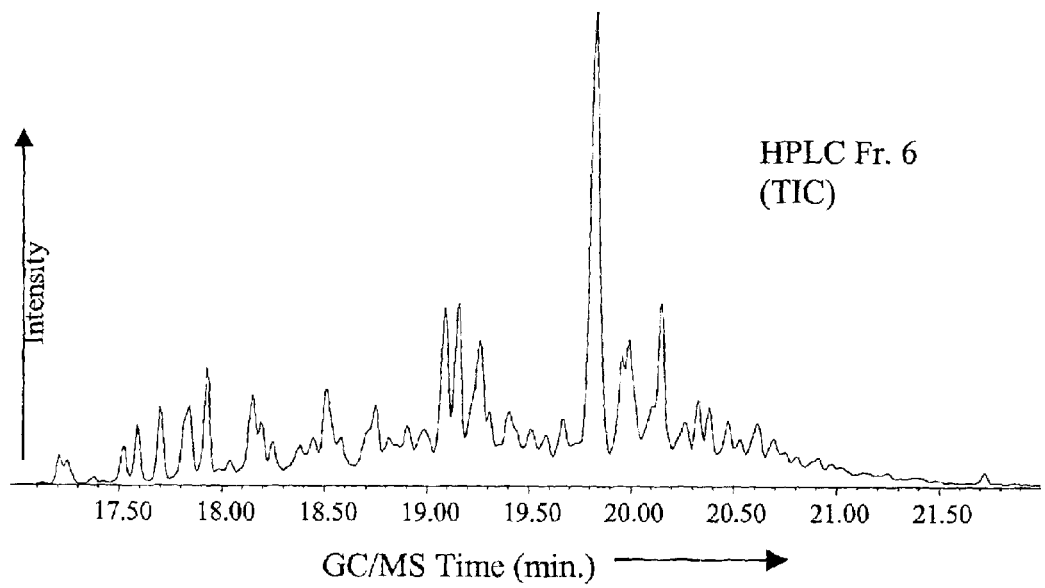
FIG. 19 illustrates GC/MS total ion current chromatogram of HPLC fraction #6 (FIG. 17), showing one major component and selected ion chromatogram of fraction #6 (m/z 292) demonstrating that this component is one of the tetramantane isomers.
Figure 19:
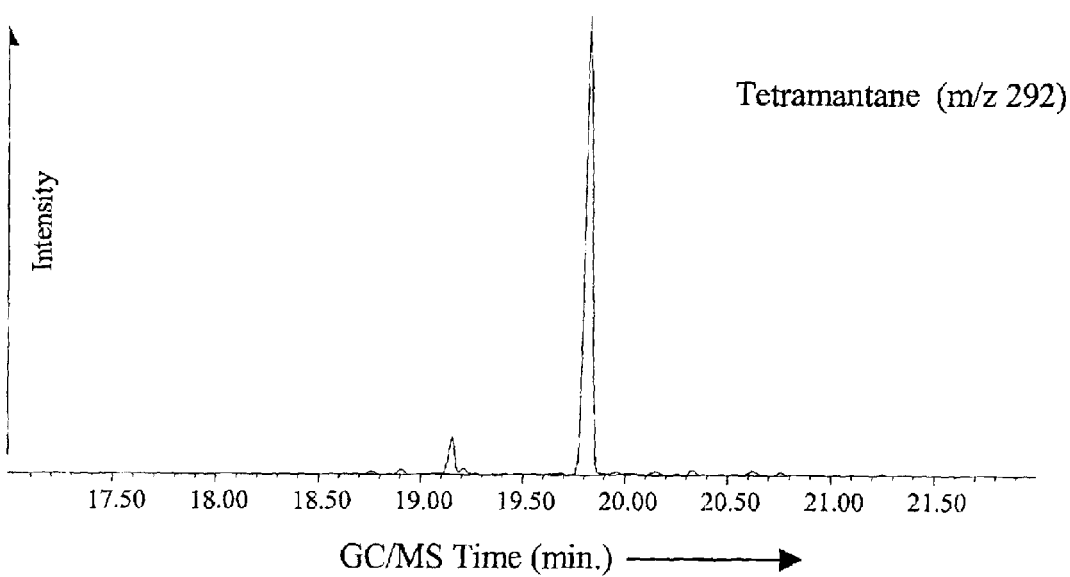

FIG. 18 compares the gas chromatogram of the starting material (Feedstock A, distillation Fraction #32) and HPLC fraction #6, from FIG. 17. HPLC Fraction #6 is significantly enriched in a tetramantane (see GC/MS FIG. 19) and is approaching a concentration sufficient to bring about its crystallization.

Example 3

Isolation of Higher Diamondoids Using Pyrolysis

Following the procedure in Example 2, (using a high-pressure/high-temperature reactor to pyrolyze and destroy undesired nondiamondoid components and concentrate the diamondoids in a distillate) gas chromatography (FID) was conducted on distillate fraction #6 (Table 3B) obtained from Feedstock B–Atmospheric distillation 650° F.+bottoms prior to pyrolysis. The feedstock is shown as a gaussian curve labeled Fr#6 in FIG. 20. Also displayed in FIG. 20 is the product of pyrolysis, labeled P#6. The pyrolysis process was conducted using the Parr reactor at 450° C. for 19.5 hours. The resulting pyrolysis product is shown in the gas chromatogram (FID) and plotted on FIG. 20. This is also shown in FIG. 21.

A comparison of the feedstock and the pyrolysis product (FIGS. 20 and 21) shows that pyrolysis has removed major non-diamondoid hydrocarbons and has increased the pentamantane and the hexamantane concentrations.

Example 4
Comparison of Feedstreams and Isolation Procedures

This example illustrates isolation procedures to concentrate the higher diamondoids for further separations using different feedstocks.

Table 5 illustrates the concentration of higher diamondoids in select gas condensates rich in diamondoids compared to the concentration of higher diamondoids found in typical petroleum. Gas condensates from the Jurassic sandstone reservoirs of the Norphlet Formation, Gulf Coast and in the LeDuc Formation, Canada have high initial diamondoid concentrations including higher diamondoids. Generally, a typical petroleum crude oil contains adamantanes present in a concentration of about 200 to 400 ppm. Of these higher diamondoids are about 0.5 weight percent of the entire amount of diamondoids in a typical crude oil.

TABLE 5

Comparison of Higher Diamondoid Concentration in Typical Petroleum vs. Select Gas Condensates Rich in Diamondoids

| Starting Material | Concentration of Higher Diamondoids (tetramantanes and higher) |
| --- | --- |
| Typical Petroleum | ~1 ppm or lower |
| Select Gas Condensates Rich in Diamondoids | 2500 ppm |

Other suitable feedstocks can also be found in refinery streams from crude oil processing. The concentrations of higher diamondoids in each refinery stream will depend on the type of crude oil and refinery operations including the distillation cut points, catalysts used and other processing operations (e.g. coking) that can increase higher diamondoid concentrations. These further processed refinery streams are identified as potential feedstocks for higher diamondoid isolations.

Table 6 illustrates the increases in higher diamondoid concentrations from initial isolation procedures of the feedstock. Such isolations can be atmospheric distillation, vacuum distillation, flash separation or other separation method known to those skilled in the art. Additionally, this treated product can further be coupled with another separation process such as pyrolytic processing.

TABLE 6

Comparison of Select Initial Isolation Procedures Used in Typical Petroleum and Diamondoid Enriched Condensate Isolations

| Initial Isolation Procedures for the Higher Diamondoids Fraction | Concentration of Higher Diamondoids (typical petroleum) | Concentration of Higher Diamondoids (gas condensate) |
| --- | --- | --- |
| Atmospheric Distillation | ~1 ppm to ~100 ppm | >95 wt. |
| Atmospheric Distillation and Pyrolytic Processing, and Isolation of Saturated Hydrocarbons by Liquid Chromatography | >50 wt. % | >50 wt. % |

The concentration measurements outlined in Table 6 are dependent upon the weight percent atmospheric distillation residue (residue after a 650° F. (345° C.) distillation at atmospheric pressure). Higher diamondoids are present in the atmospheric distillation residue of crude oils, and the weight percent of atmospheric residual in a crude oil can vary from about ~1percent to less than about ~80weight percent.

While Table 6 illustrates a combination of atmospheric distillation and pyrolytic processing, pyrolytic processing (thermal destruction of non-diamondoids) can be performed on un-distilled feed stock or vacuum distillate fractions. If so, the pyrolytically treated feedstock can then be subjected to removal of lower diamondoids.

Secondary isolation procedures could include either vacuum distillation used alone or in combination with liquid chromatography.

Fractionation of the atmospheric residue can also be performed prior to the pyrolytic processing.

Some overlap of higher diamondoid series occurs between distillation cuts, for example, the most structurally condensed hexamantane isomer distills at lower temperatures than other hexamantanes and is found in the pentamantane containing distillation fractions. Likewise, the most condensed isomers of the heptamantane series distills with the uncondensed hexamantanes, and so on. Furthermore, as the number of isomers increase with each successive higher diamondoid series, boiling point distributions of isomers spread out with progressively more overlap of series occurring as molecular weights increase. Additionally, substituent groups on the isomers will effect the distillation fractions.

A tertiary isolation procedure can be used to further purify the products from the secondary isolation procedure or can be used in place of the secondary. For example, liquid chromatography can be use to remove aromatic hydrocarbons.

The tertiary isolation procedures comprises as examples, preparative Gas Chromatography and High Performance Liquid Chromatography. Other suitable separation technologies are known to those skilled in the art. These tertiary isolation procedures generate mixtures from which individual compounds can generally, but not always be crystallized for recovery. The highest purity values of Table 7 assume crystallization. Methods such as zone refining and vacuum sublimation can yield materials of much greater purities.

TABLE 7

Purity of Individual Higher Diamondoids Obtained from Tertiary Isolation Procedures

| Tertiary Isolation Procedures of Individual Tetramantanes, Pentamantanes, Hexamantanes, etc., Fractions | Purity of Tetra-mantanes | Purity of Penta-mantanes | Purity of Hexa-mantanes | Purity of Hepta-mantanes | Purity of Octa-mantanes | Purity of Nona-Mantanes | Purity of Deca-mantanes |
|---|---|---|---|---|---|---|---|
| Preparative Gas Chromatography | >99.9 | >99.9 | >99.9 | >99.9 | >99.9 | >99.9 | >99.9 |
| High Performance Liquid Chromatography | >30 – 99.9 | >20 – 99.9 | >10 – 99.9 | >5 – 99.9 | >2 – 99.9 | >1 – 99.9 | 1 > –99.9 |

Example 5
Enrichment of Pentamanatanes, Hexamantanes and Heptamantanes

A sample of the distillate fraction #5 (Table 3B) from Feedstock B–Atmospheric distillation 650° F.+bottoms, in the amount of (5.23 g), was sealed in an evacuated pressure vessel and heated at 450° C. for 16.7 hours. After 16.7 hours the vessel was cooled, vented, and the contents extracted with cyclohexane, yielding 0.46 g of extract. Carbon residue was present in the reaction vessel. The extract was separated into saturated and aromatic hydrocarbon fractions using liquid chromatography (10 weight % silver nitrate on silica gel absorbent and cyclohexane eluent).

Figure 22:
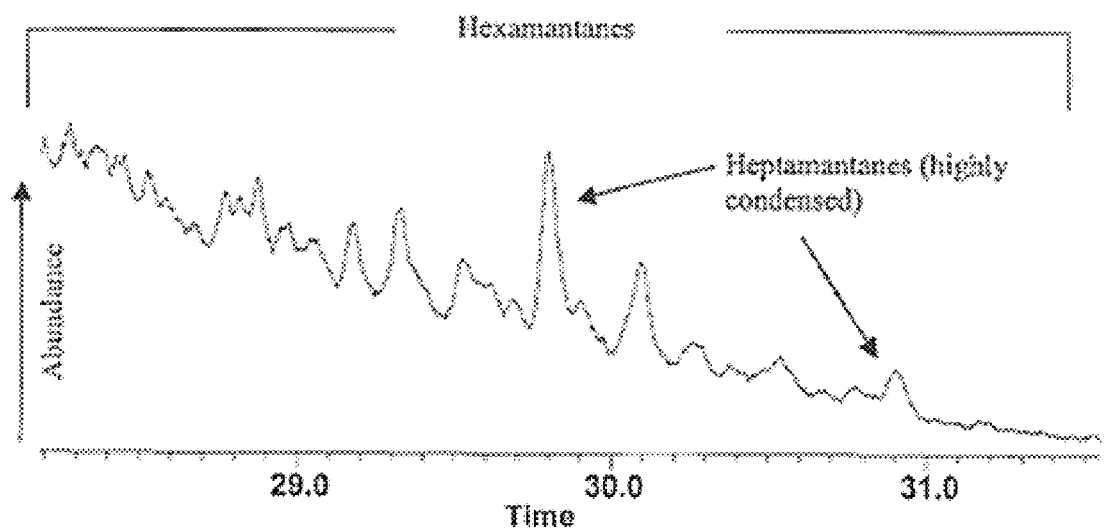
FIG. 22 illustrates an enlarged segment of the gas chromatogram of FIG. 21, from approximately 22 to 35 minutes, and the resulting hexamantanes and highly condensed heptamantanes available for isolation.

FIG. 21 compares gas chromatograms of the starting material and process product, showing that the non-diamondoid components have been removed; the large bell-shaped distribution of non-diamondoids hydrocarbons centered around 27 min. in the starting material (FIG. 21, top) has been completely removed from the product (FIG. 21 bottom). FIG. 22 shows an expansion of the 28.2 to 31.5 region of the bottom chromatogram in FIG. 21. Peaks in FIG. 22 included pentamantes, hexamantanes and two highly condensed heptamantanes. Nondiamondoid compounds were not detected.

Example 6
Isolation of Pentamantanes

A distillation fraction containing pentamantanes was processed using preparative capillary gas chromatography to exemplify the isolation of pentamantane.

The distillation fraction 38 was prepared by the distillation of gas condensate Feedstock A, and was treated by liquid chromatography (10% silver nitrate on silica gel) to remove all but the saturated hydrocarbons. The preparative gas chromatographic fraction collector was set to collect material associated with a peak identified as a pentamantane isomer by gas chromatography mass spectroscopy (GC/MS).

The preparative gas chromatograph used two capillary columns to effect separation of the pentamantane. The distillate fraction sample in cyclohexane solution was injected (1 microliter) into a first gas chromatographic column with the inlet operating in splitless mode. The sample was separated utilizing the (nonpolar) gas chromatographic column and the chromatographic peak corresponding to the target pentamantane was shunted to a second (polar) chromatographic column to further separate the target pentamantane. The material shunted to the second column was further cut and the product sent to a fraction collector, thus trapping two isolated pentamantane.

The preparative gas chromatograph is computer assisted and can be operated in an automated mode so that multiple preparative chromatographic runs can be completed.

Figure 23:
FIG. 23 illustrates a photomicrograph two co-crystallized pentamantane from Feedstock A.

When sufficient pentamantane was isolated in the collector trap, the trap was removed from the chromatograph and the two pentamantanes were dissolved in cyclohexane and crystallized. FIG. 23 shows a crystal approximately 250 micron in diameter that was dissolved in cyclohexane and recrystalized. It consists of two pentamantanes which co-crystalize.

Example 7
Isolation of Higher Diamondoids

The distillation fractions of the atmospheric residue of Feedstock B were prepared for isolation of high molecular weight members of the higher diamondoids. The distillate fraction #6 from Feedstock B–Atmospheric distillation 650° F.+bottoms was processed using the pyrolytic methods disclosed in Example 5 to thermally degrade a portion of the non-diamondoid components.

The product of the pyrolytic process was further processed by liquid chromatography over silver nitrate impregnated silica gel to remove any remaining polar or aromatic components. This product was then examined by gas chromatography-mass spectrometry (GS/MS) for the presence of uncondensed heptamantanes, condensed octamantanes, partially condensed nonamantanes or a unique highly condensed decamantane.

Figure 24:
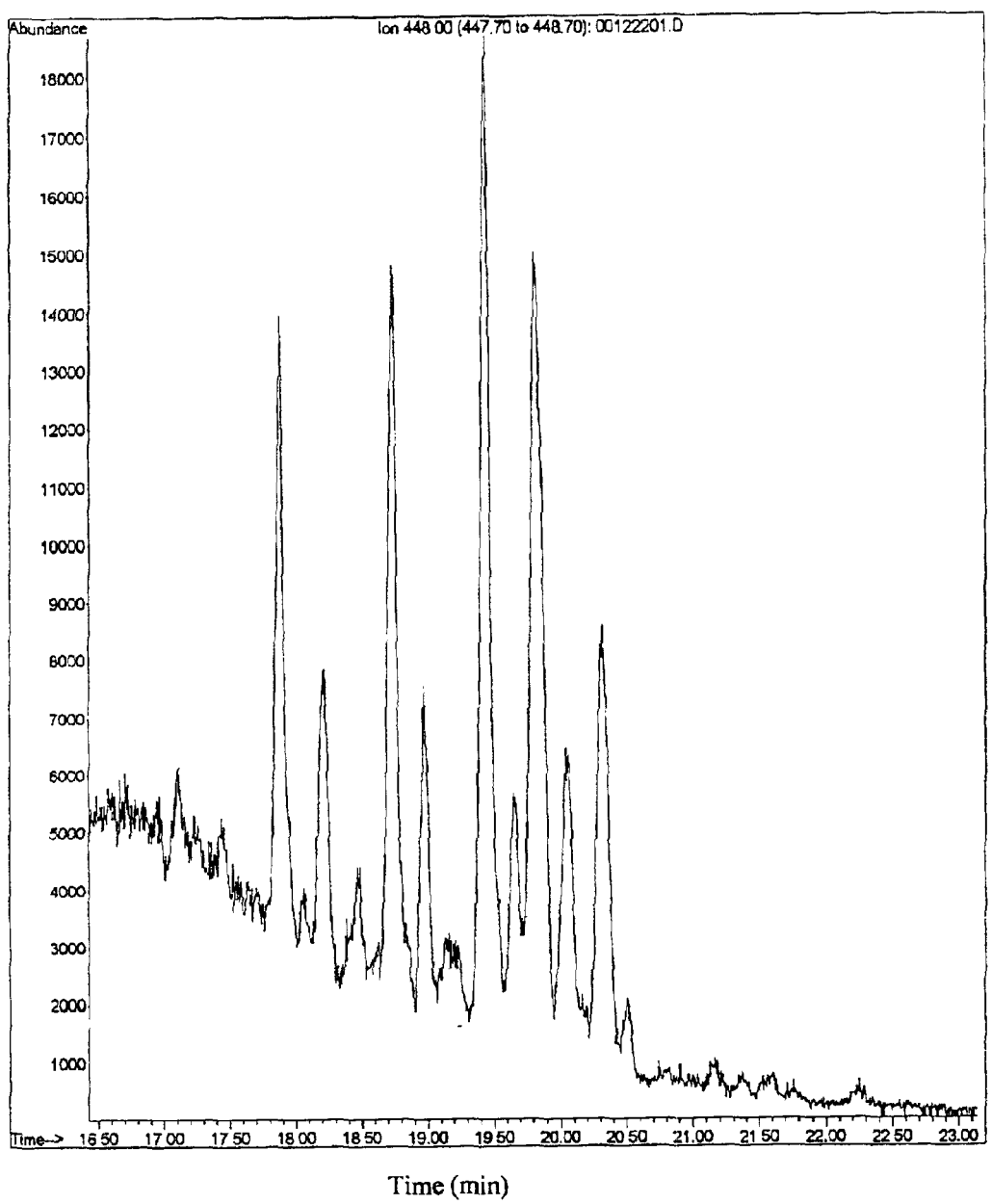
FIG. 24 illustrates a mass spectra of the distillate fraction #6, Feedstock B 650° F.+distillation bottoms, pyrolysis product showing the presence of mol. wt. 448 heptamantanes purified therefrom.
Figure 25:
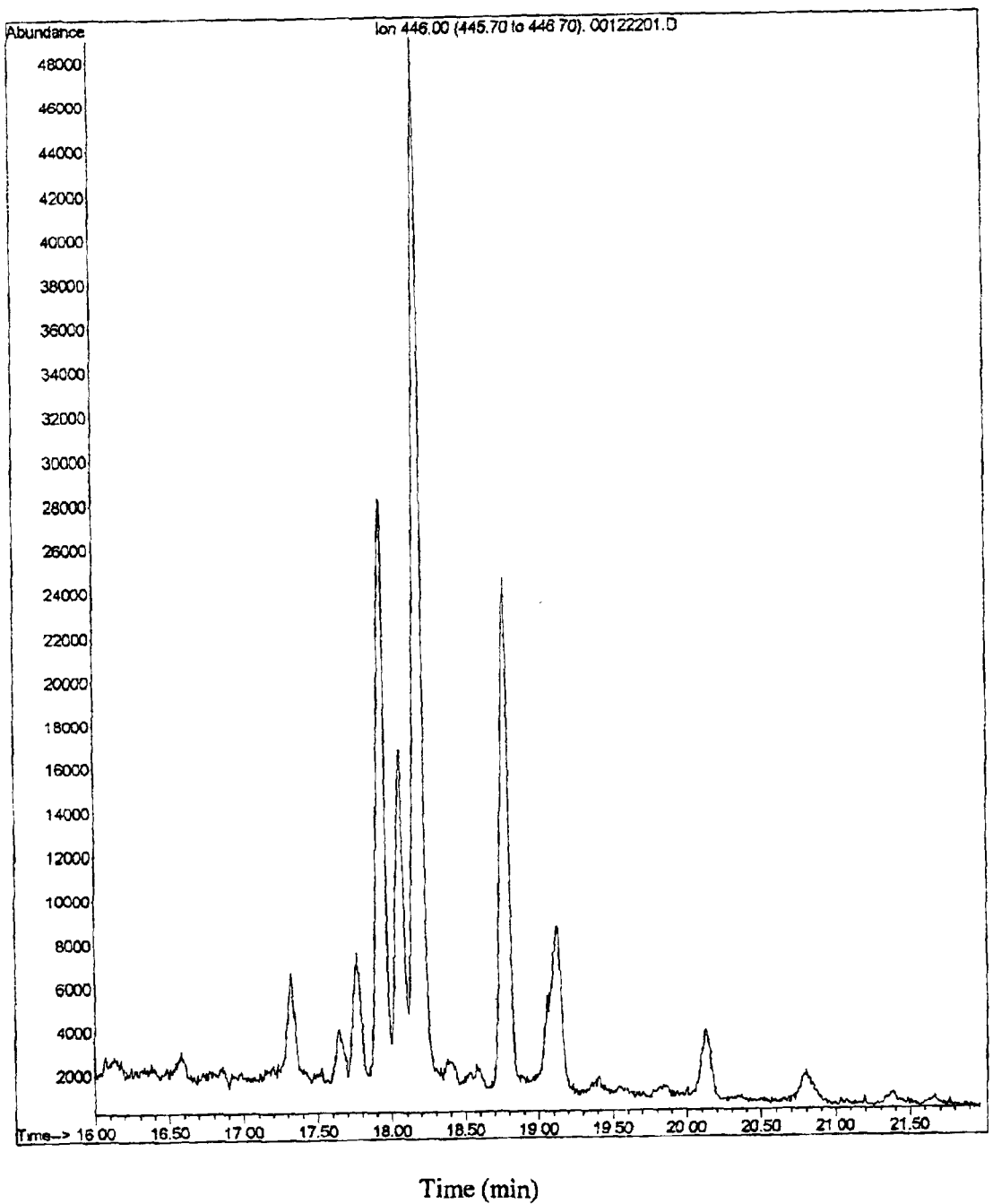
FIG. 25 illustrates a mass spectra of the distillate fraction #6, Feedstock B 650° F.+distillation bottoms, pyrolysis product showing the presence of mol. wt. 446 octamantanes purified therefrom.
Figure 26:
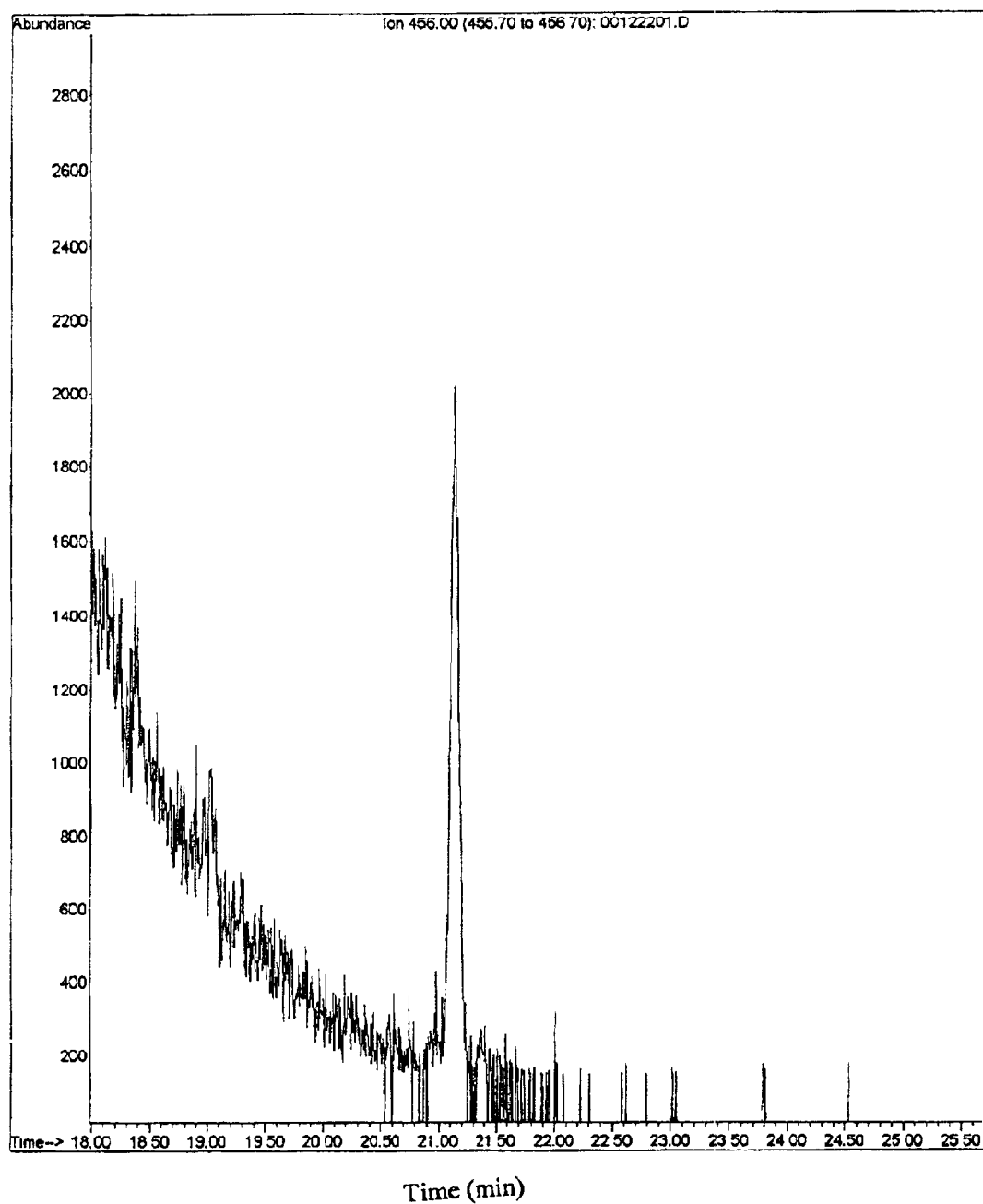
FIG. 26 illustrates a mass spectra of the distillate fraction #6, Feedstock B 650° F.+distillation bottoms, pyrolysis product showing the presence of the most mol. wt. 456 decamantane purified therefrom.

Evidence for the presence of these higher diamondoids is shown in the ion chromatograms illustrated in FIGS. 24–26. Specifically, FIG. 24 shows the uncondensed heptamantanes at m/z 448; FIG. 25 shows the condensed octamantanes at m/z 446; FIG. 26 shows the highly condensed decamantane at m/z 456.

From the foregoing description, various modifications and changes in the above methods will occur to those skilled in the art. All such modifications within the claims are intended to be included therein.

Example 8
Isolation and Crystallization of Higher Diamondoids

The distillate fraction #6 from Feedstock B–Atmospheric distillation 650° F.+bottoms was processed using the pyrolytic methods disclosed in Example 5 to thermally degrade a portion of the non-diamondoid components. A sample consisting of 15 grams of distillate fraction #6 was treated in the reaction vessel for 19.5 hours at 450° C. to thermally degrade the non-diamond components. The resulting pyrolytic product was eluted with cyclohexane on a gravity column over silver nitrate impregnated silica gel to remove any remaining polar or aromatic compounds. The concentrated diamondoid product was subjected to preparative gas chromatography as outlined in Example 1 for isolation of individual higher diamondoids as identified by mass spectrometry.

Figure 27:
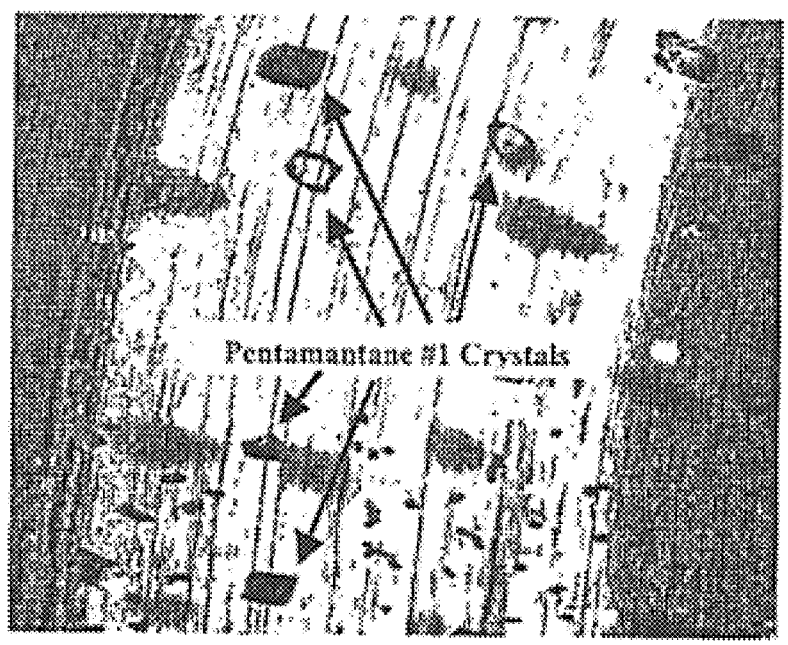
FIG. 27A is a photomicrograph of crystals of pentamantane #1 (mol. wt. 344) isolated from Feedstock B by preparative capillary gas chromatography.
FIG. 27B is a GC/MS total ion current chromatogram and 27C is the mass spectrum showing the purity of this isolated pentamantane.
Figure 27:
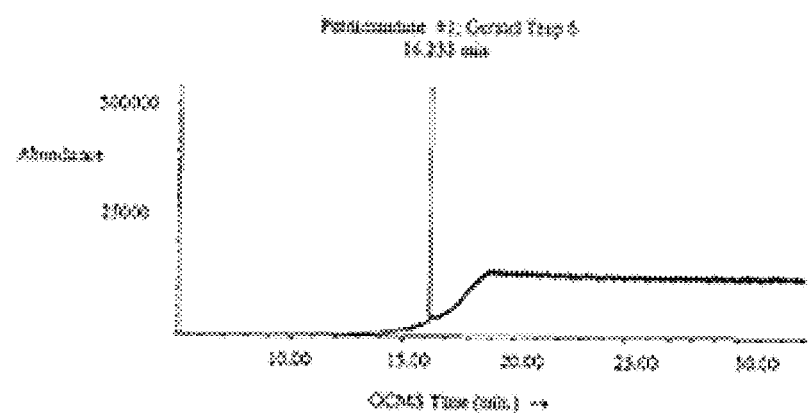
Figure 27:
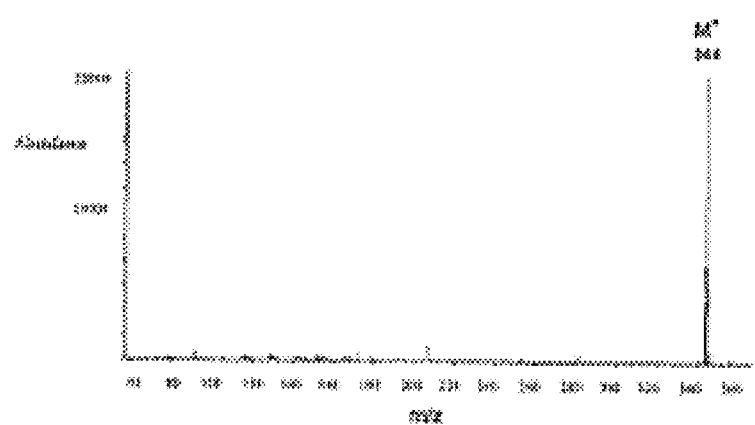
Figure 28:
FIG. 28A is a photomicrograph of crystals of hexamantane #8 (mol. wt. 396) isolated from Feedstock B by preparative capillary gas chromatography.
FIG. 28B is a GC/MS total ion current chromatogram and 28C is the mass spectrum showing the purity of this isolated hexamantane.
Figure 28:
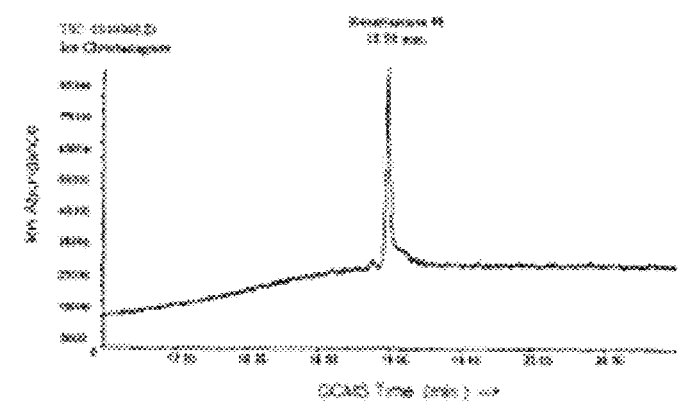
Figure 28:
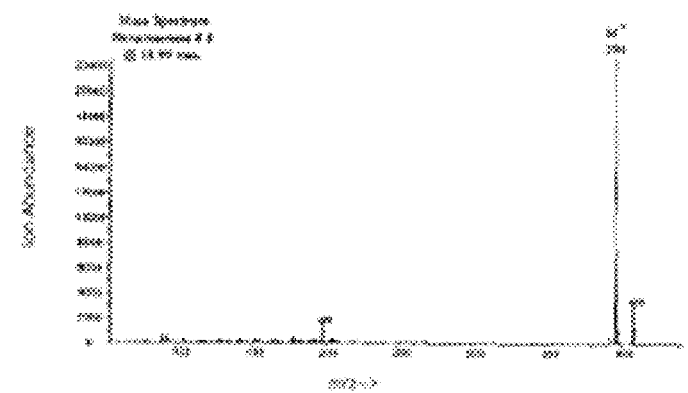
Figure 29:
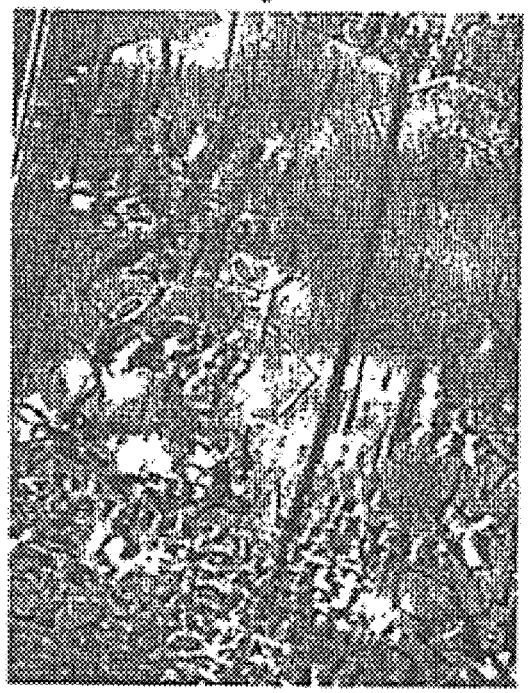
FIG. 29A is a photomicrograph of crystals of a fully condensed heptamantane (mol. wt. 394) isolated from Feedstock B by preparative capillary gas chromatography.
FIG. 29B is a GC/MS total ion current chromatogram and 29C is the mass spectrum showing the purity of this isolated heptamantane.
Figure 29:
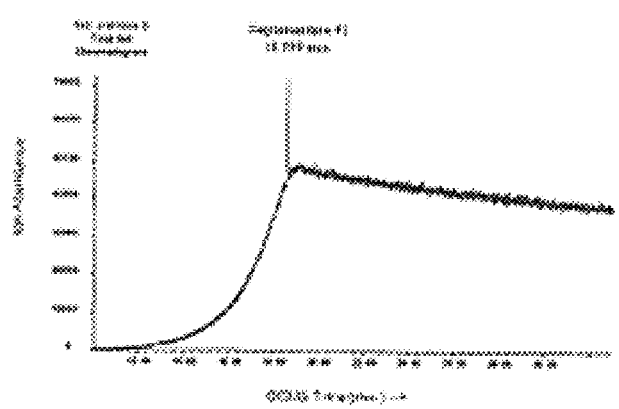
Figure 29:
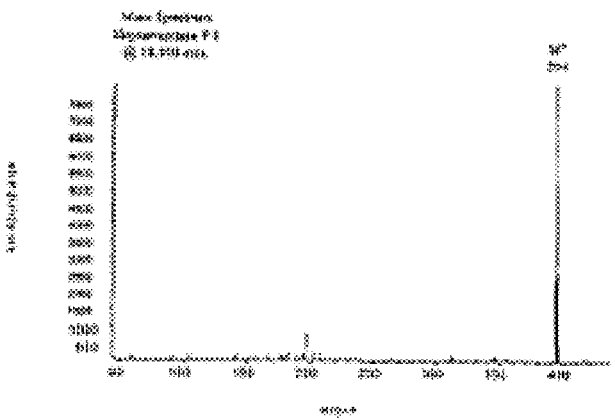

At least one of the following higher diamondoid components were isolated and crystallized as illustrated in FIGS. 27–29. FIG. 27 is a photomicrograph and mass spectrum of crystals of a single pentamantane (mol. wt. 344) isolated from Feedstock B; FIG. 28 is a photomicrograph and mass spectrum of crystals of a single hexamantane (mol. wt. 396) isolated from Feedstock B; and FIG. 29 is a photomicrograph and mass spectrum of crystals of a single condensed heptamantane (mol. wt. 394) isolated from Feedstock B.

Example 9
Multiple Column HPLC Enrichment of Higher Diamondoid

Higher diamondoids can be isolated in high purity by using HPLC methods employing a single column (as shown for the tetramantanes, see FIGS. 17 and 18). However, an excellent method for isolating high-purity higher diamondoids uses two or more HPLC columns of different selectivities used in succession. (FIG. 32 Hexa ODS HPLC Chart) shows results of a preparative ODS HPLC separation (with acetone as a mobile phase) of the 396 molecular weight hexamantanes from a saturated hydrocarbon fraction of a pyrolysis product prepared from Feedstock B, FSL 8691 distillation cut #6.

This first HPLC system consisted of two Whatman M20 10/50 ODS columns operated in series using acetone as mobile phase at 5.00 mL/min. From this HPLC run (FIG. 32 Hexa ODS HPLC Chart) fractions 36 and 37 were combined and taken for further purification on a second HPLC system. This combined fraction (36 and 37) contained hexamantane #7, 11 and 13.

Further purification of this combined ODS HPLC fraction was achieved using a HYPERCARB stationary phase HPLC column having a different selectivity in the separation of various hexamantanes than the ODS column discussed above. (FIG. 33 Hexa Hypercarb HPLC Chart) shows elution times of the individual hexamantanes on the Hypercarb HPLC column (with acetone as a mobile phase).

Figure 33:
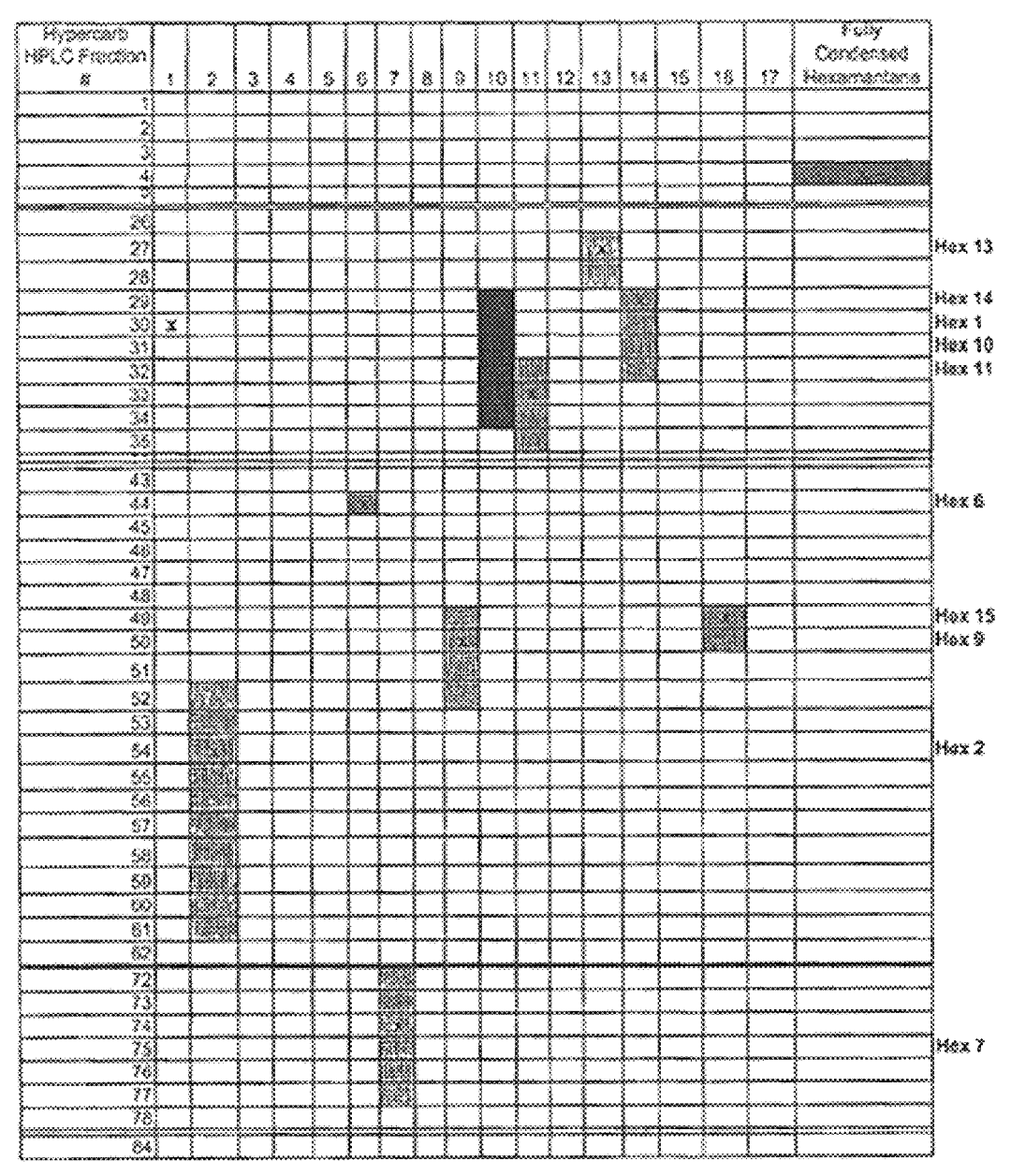

The differences in elution times and elution order of hexamantanes on ODS and Hypercarb HPLC are seen by comparing these two Figures. For example, Hexamantanes #11 and 13 elute together on the ODS HPLC system (FIG. 32 Hexa ODS HPLC Chart) but in separate fractions (fractions 32 and 27, respectively) on the Hypercarb system (FIG. 33 Hexa Hypercarb HPLC Chart).

By relying on the different elution order/times of these HPLC systems, fractions showing impurities or co-elution of higher diamondoids can be further purified by using an appropriate column of the different selectivities. Using this method combined ODS HPLC fractions 36 & 37, appropriate Hypercarb HPLC fractions were taken from a Hypercarb HPLC run thus providing high-purity hexamantane #13. Other ODS HPLC fractions and Hypercarb HPLC cut points could be used to isolate the remaining hexamantanes.

The ODS and Hypercarb columns can also be used in reverse order for these isolations. By using similar methodology as above, i.e. fractionating hexamantane-containing ODS fractions using the Hypercarb or other suitable column and collecting at corresponding elution times can lead to the isolation of the remaining hexamantanes in high purity. This is also true of all of the other higher diamondoids from tetramantanes to undecamantanes, including substituted forms.

What is claimed is:

1. A process for recovering a composition enriched in tetramantane components and other higher diamondoid components which process comprises:
   a. selecting a feedstock comprising recoverable amounts of tetramantane components and other higher diamondoid components;
   b. removing a sufficient amount of components from the feedstock having a boiling point less than the lowest boiling point tetramantane component under conditions wherein recoverable amounts of tetramantane components and other higher diamondoid components are retained in the treated feedstock; and
   c. thermally treating the feedstock recovered in b) above to pyrolyze at least a sufficient amount of nondiamondoid components therefrom to permit recovery of tetramantane components and other higher diamondoid components from the pyrolytically treated feedstock wherein said pyrolysis is conducted under conditions to provide for a treated feedstock retaining recoverable amounts of tetramantane components and other higher diamondoid components.

2. A process for recovering a composition enriched in tetramantane components and other higher diamondoid components which process comprises:
   a. selecting a feedstock comprising recoverable amounts of tetramantane components and other higher diamondoid components, non-diamondoid components having a boiling point both below and above the lowest boiling point tetramantane component, and at least one lower diamondoid component;
   b. removing a sufficient amount of non-diamondoid components having a boiling point below the lowest boiling point tetramantane component as well as lower diamondoid components from the feedstock under conditions to provide a treated feedstock wherein tetramantane components and other higher diamondoid components are retained therein; and
   c. thermally treating said treated feedstock recovered in b) to pyrolyze at least a sufficient amount of non-diamondoid components therefrom to permit recovery of tetramantane components and other higher diamondoid components from the pyrolytically treated feedstock.

3. A process for recovering a composition enriched in tetramantane components and other higher diamondoid components which process comprises:
   a. selecting a feedstock comprising recoverable amounts of tetramantane components and other higher diamondoids components;
   b. thermally treating the feedstock to pyrolyze at least a sufficient amount of non-diamondoid components therefrom to permit recovery of tetramantane and other higher diamondoid components from the pyrolytically treated feedstock wherein said pyrolysis is conducted under conditions to provide for a treated feedstock retaining recoverable amounts of tetramantane components and other higher diamondoid components; and
   c. removing a sufficient amount of those components from the feedstock surviving pyrolysis which components have a boiling point less than the lowest boiling point tetramantane component under conditions wherein recoverable amounts of tetramantane components and other higher diamondoid components are retained in the treated feedstock.

4. A process for recovering a composition enriched in tetramantane components and higher diamondoid components which process comprises:

a. selecting a feedstock comprising recoverable amounts of tetramantane components and other higher diamondoid components, non-diamondoid components, and at least one lower diamondoid component;

b. thermally treating said feedstock to pyrolyze at least a portion of the non-diamondoid components under conditions wherein recoverable amounts of tetramantane components and other higher diamondoid components are retained in said pyrolytically treated feedstock; and c. removing a sufficient amount of lower diamondoid components from the pyrolytically treated feedstock under conditions to provide a treated feedstock from which tetramantane components and other higher diamondoid components can be recovered.

5. The process of claim 2 or 4 wherein sufficient amounts of lower diamondoid components are removed from the feedstock to provide for a treated feedstock comprising a ratio of the amount of lower diamondoid components to higher diamondoid components of about 9:1 or less.

6. The process of claim 5 wherein sufficient amounts of lower diamondoid components are removed from the feedstock to provide for a treated feedstock comprising a ratio of the amount of lower diamondoid components to the amount of higher diamondoid components of about 2:1 or less.

7. The process of claim 6 wherein sufficient amounts of lower diamondoid components are removed from the feedstock to provide for a treated feedstock comprising a ratio of the amount of lower diamondoid components to the amount of higher diamondoid components of about 1:1 or less.

8. The process according to claim 1 or 2 wherein at least about 10% of said tetramantane components and higher diamondoid components are retained in the feedstock after procedure (b) as compared to that amount of such components present prior to said procedure.

9. The process according to claim 8 wherein at least about 50% of said tetramantane components and other higher diamondoid components are retained in the feedstock after procedure (b) as compared to that amount of such components present prior to said procedure.

10. The process according to claim 9 wherein at least about 90% of said tetramantane components and other higher diamondoid components are retained in the feed stock after procedure (b) as compared to that amount of such components present prior to said procedure.

11. The process according to claim 1, 2, 3 or 4 wherein at least about 10% of said tetramantane components and other higher diamondoid components are retained in the feedstock after pyrolysis as compared to that amount present prior to pyrolysis.

12. The process according to claim 11 wherein at least about 50% of said tetramantane components and other higher diamondoid components are retained in the feedstock after pyrolysis as compared to that amount present prior to pyrolysis.

13. The process of claim 1, 2, 3 or 4 wherein said feedstock comprises at least about 1 ppb of tetramantane components and higher diamondoid components.

14. The process of claim 1, 2, 3 or 4 wherein removal of non-diamondoid components and/or lower diamondoid components from the feedstock comprises distilling said feedstock.

15. The process of claim 14 wherein at least about 50 weight percent of the lower diamondoid components, based on the total weight of lower diamondoid components present in the untreated feedstock, is removed.

16. The process of claim 1, 2, 3 or 4 which further comprises recovering tetramantane and other higher diamondoid components from the product of step c) by use of one or more separation techniques selected from the group consisting of chromatographic techniques, thermal diffusion techniques, crystallization, sublimation, and size separation techniques.

17. The process of claim 16 wherein said separation technique is a chromatographic technique.

18. The process of claim 17 wherein said chromatographic technique is selected from the group consisting of liquid chromatography, gas chromatography and high performance liquid chromatography.

19. The process of claim 1, 2, 3 or 4 wherein the product of step c) comprises at least 10 weight percent of non-ionized tetramantane components and higher diamondoid components and at least 0.5 weight percent of non-ionized pentamantane components and higher diamondoid components based on the total weight of diamondoid components present.

20. The process of claim 1, 2, 3 or 4 wherein the product of step c) comprises at least 10 weight percent of non-ionized tetramantane components and higher diamondoid components and at least 0.5 weight percent of non-ionized pentamantane components and higher diamondoid components based on the total weight of the recovered feedstock.

21. A process for recovering a composition enriched in tetramantane and pentamantane components which process comprises:

a. selecting a feedstock comprising recoverable amounts of tetramantane and pentamantane components;

b. removing a sufficient amount of components from the feedstock having a boiling point less than the lowest boiling tetramantane component under conditions to provide a treated feedstock from which tetramantane and pentamantane components can be recovered; and c. recovering tetramantane and pentamantane components from said treated feedstock by separation techniques selected from the group consisting of chromatographic techniques, thermal diffusion techniques, zone refining, progressive recrystallization and size separation techniques.

22. A composition comprising at least tetramantane and pentamantane components wherein said composition comprises at least about 10 weight percent tetramantane components and at least 0.5 weight percent pentamantane components based on the total weight of diamondoid components present.

23. A composition comprising at least tetramantane and pentamantane components wherein said composition comprises at least about 25 weight percent tetramantane components and at least 0.5 weight percent pentamantane components based on the total weight of diamondoid components present.

24. A composition comprising at least tetramantane and pentamantane components wherein said composition comprises at least about 50 weight percent tetramantane components and at least 0.5 weight percent pentamantane components based on the total weight of diamondoid component present.

25. The composition of claim 22, 23 or 24 wherein said compositions further comprise hexamantane.

26. A composition comprising at least tetramantane and pentamantane components wherein said composition comprises at least about 10 weight percent tetramantane components and at least 0.5 weight percent pentamantane components based on the total weight of the composition.

27. A composition comprising at least tetramantane and pentamantane components wherein said composition comprises at least about 25 weight percent tetramantane components and at least 0.5 weight percent pentamantane components based on the total weight of the composition.

28. A composition comprising at least tetramantane and pentamantane components wherein said composition comprises at least about 50 weight percent tetramantane components and at least 0.5 weight percent pentamantane components based on the total weight of the composition.

29. The composition of claim 26, 27 or 28 wherein said compositions further comprise hexamantane.

30. A process which comprises:
   a. selecting a feedstock comprising recoverable amounts of a higher diamondoid component or components selected for recovery, nondiamondoid components and components having a boiling point less than the lowest boiling point higher diamondoid component selected for recovery;
   b. removing from the feedstock a sufficient amount of components having a boiling point less than the lowest boiling point higher diamondoid component selected for recovery under conditions wherein recoverable amounts of the higher diamondoid component or components selected for recovery are retained in the treated feedstock; and
   c. thermally treating the feedstock recovered in b) above to pyrolyze at least a sufficient amount of nondiamondoid components therefrom to permit recovery of the selected higher diamondoid component or components from the pyrolytically treated feedstock wherein the pyrolysis is conducted under conditions to provide a treated feedstock retaining recoverable amounts of the selected higher diamondoid component or components.

31. A process for recovering a composition enriched in higher diamondoid components which process comprises:
   a. selecting a feedstock comprising recoverable amounts of a selected higher diamondoid component or components, nondiamondoid components having a boiling point both below and above the lowest boiling point selected higher diamondoid component, and at least one lower diamondoid component;
   b. removing a sufficient amount of lower diamondoid component and nondiamondoid components having a boiling point below the lowest boiling point selected higher diamondoid component as well as lower diamondoid components from feedstock under conditions to provide a treated feedstock wherein the selected higher diamondoid component or components are retained therein; and
   c. thermally treating said treated feedstock recovered in b) to pyrolyze at least a sufficient amount of nondiamondoid components therefrom to permit recovery of the selected higher diamondoid components from the pyrolytically treated feedstock.

32. A process for recovering a composition enriched in a selected higher diamondoid component or components which process comprises:
   a. selecting a feedstock comprising recoverable amounts of a selected higher diamondoid component or component, nondiamondoid components and components having a boiling point less than the lowest boiling point higher diamondoid component selected for recovery;
   b. thermally treating said feedstock to pyrolyze at least a sufficient amount of nondiamondoid components under therefrom to permit recovery of the selected higher diamondoid component or components from the pyrolytically treated feedstock wherein said pyrolysis is conducted under conditions to provide for a treated feedstock retaining recoverable amounts of the selected higher diamondoid component or components; and
   c. removing a sufficient amount of those components from the feedstock surviving pyrolysis which components have a boiling point less than the lowest boiling point selected higher diamondoid component under conditions wherein recoverable amounts of the selected higher diamondoid component or components are retained in the treated feedstock.

33. A process for recovering a composition enriched in a selected higher diamondoid component or components which process comprises:
   a. selecting a feedstock comprising recoverable amounts of a selected higher diamondoid component or components, nondiamondoid components and at least one lower diamondoid component;
   b. thermally treating said feedstock to pyrolyze at least a portion of the nondiamondoid component under conditions wherein recoverable amounts of the selected higher diamondoid component or components are retained in said pyrolytically treated feedstock; and
   c. removing a sufficient amount of lower diamondoid components from the pyrolytically treated feedstock under conditions to provide a treated feedstock from which the selected higher diamondoid component or components can be recovered.

34. A process for recovering a composition enriched in one or more selected higher diamondoid components which process comprises:
   a. selecting a feedstock comprising recoverable amounts of one or more selected higher diamondoid components and nonselected materials;
   b. removing from the feedstock a sufficient amount of nonselected materials having boiling points less than the lowest boiling point selected higher diamondoid component under conditions to form a treated feedstock enriched in selected higher diamondoid components which can be recovered; and
   c. recovering a composition enriched in one or more selected higher diamondoid components from said treated feedstock formed in b) above with one or more additional separation techniques selected from the group consisting of chromatographic techniques, thermal diffusion techniques, zone refining, progressive recrystallization and size separation techniques.

35. A process for recovering a composition enriched in one or more selected higher diamondoid components which process comprises:
   a. selecting a feedstock comprising recoverable amounts of one or more selected higher diamondoid components and nonselected materials including nondiamondoid components;
   b. removing from the feedstock a sufficient amount of nonselected materials having a boiling point less than the lowest boiling point selected higher diamondoid component under conditions to form a treated feedstock enriched in selected higher diamondoid components which can be recovered;
   c. thermally degrading said treated feedstock to pyrolyze at least a sufficient amount of nondiamondoid components therefrom under conditions to form a thermally treated feedstock retaining recoverable amounts of selected higher diamondoid; and d. recovering a composition enriched in one or more selected higher diamondoid components from said thermally treated feedstock formed in c) above with one or more additional separation techniques selected from the group consisting of chromatographic techniques, thermal diffusion techniques, zone refining, progressive recrystallization and size separation techniques.

36. A process for recovering a composition enriched in one or more selected higher diamondoid components which process comprises:
   a. selecting a feedstock comprising recoverable amounts of one or more selected higher diamondoid components and nonselected materials including nondiamondoid components;
   b. thermally degrading said feedstock to pyrolyze at least a sufficient amount of nondiamondoid components therefrom under conditions to provide a thermally treated feedstock retaining recoverable amounts of selected higher diamondoid;
   c. removing from the thermally treated feedstock a sufficient amount of nonselected materials having a boiling point less than the lowest boiling point of selected higher diamondoid component under conditions to form a treated feedstock enriched in selected higher diamondoid components which can be recovered; and
   d. recovering a composition enriched in one or more selected higher diamondoid components from said treated feedstock recovered in c) above with one or more additional separation techniques selected from the group consisting of chromatographic techniques, thermal diffusion techniques, zone refining, progressive recrystallization and size separation techniques.

37. A process for recovering a composition enriched in one or more selected higher diamondoid components which process comprises:
   a. selecting a feedstock comprising recoverable amounts of one or more selected higher diamondoid components and nonselected materials;
   b. fractionating the feedstock to form one or more cuts enriched in materials having boiling points in the range of from just below the boiling point of the lowest boiling selected higher diamondoid component to just above the boiling point of the highest boiling selected higher diamondoid component; and
   c. recovering a composition enriched in one or more selected higher diamondoid components from said one or more cuts formed in b) above with one or more additional separation techniques selected from the group consisting of chromatographic techniques, thermal diffusion techniques, zone refining, progressive recrystallization and size separation techniques.

38. A process for recovering a composition enriched in one or more selected higher diamondoid components which process comprises:
   a. selecting a feedstock comprising recoverable amounts of one or more selected higher diamondoid components and nonselected materials including nondiamondoid components;
   b. fractionating the feedstock to form one or more cuts enriched in materials having boiling points in the range of from just below the boiling point of the lowest boiling selected higher diamondoid component to just above the boiling point of the highest boiling selected higher diamondoid component;
   c. thermally degrading one or more cuts said to pyrolyze at least a sufficient amount of nondiamondoid components therefrom under conditions to form one or more thermally treated cuts retaining recoverable amounts of selected higher diamondoid; and
   d. recovering a composition comprising one or more selected higher diamondoid components from one or more said thermally treated cuts formed in c) above with one or more additional separation techniques selected from the group consisting of chromatographic techniques, thermal diffusion techniques, zone refining, progressive recrystallization and size separation techniques.

39. A process for recovering a composition enriched in one or more selected higher diamondoid components which process comprises:
   a. selecting a feedstock comprising recoverable amounts of one or more selected higher diamondoid components and nonselected materials including nondiamondoid components;
   b. thermally degrading said feedstock to pyrolyze at least a sufficient amount of nondiamondoid components therefrom under conditions to provide a thermally treated feedstock retaining recoverable amounts of selected higher diamondoid;
   c. fractionating the thermally treated feedstock to form one or more cuts enriched in materials having boiling points in the range of from just below the boiling point of the lowest boiling selected higher diamondoid component to just above the boiling point of the highest boiling selected higher diamondoid component; and
   d. recovering a composition enriched in one or more selected higher diamondoid components from one or more cuts formed c) above with one or more additional separation techniques selected from the group consisting of chromatographic techniques, thermal diffusion techniques, zone refining, progressive recrystallization and size separation techniques.

* * * * *